(12) United States Patent
Haeussner et al.

(10) Patent No.: US 11,957,139 B2
(45) Date of Patent: Apr. 16, 2024

(54) COMPOSITIONS FOR IMPROVING NITROGEN UTILIZATION IN A RUMINANT

(71) Applicant: Evonik Operations GmbH, Essen (DE)

(72) Inventors: Thomas Haeussner, Eppertshausen (DE); Georg Borchers, Bad Nauheim (DE); Frank Fischer, Hofheim (DE); Lucas Geist, Freigericht (DE); Christoph Kobler, Alzenau (DE); Cornelia Borgmann, Frankfurt (DE); Javier Martin-Tereso Lopez, MH Amersfoort (NL); Isabela Pena Carvalho De Carvalho, MH Amersfoort (NL)

(73) Assignee: Evonik Operations GmbH, Essen (DE)

( * ) Notice: Subject to any disclaimer, the term of this patent is extended or adjusted under 35 U.S.C. 154(b) by 810 days.

(21) Appl. No.: 16/070,583

(22) PCT Filed: Jan. 19, 2016

(86) PCT No.: PCT/EP2016/051034
§ 371 (c)(1),
(2) Date: Jul. 17, 2018

(87) PCT Pub. No.: WO2017/125140
PCT Pub. Date: Jul. 27, 2017

(65) Prior Publication Data
US 2020/0288751 A1   Sep. 17, 2020

(51) Int. Cl.
*A23K 40/35* (2016.01)
*A23K 20/158* (2016.01)
*A23K 50/15* (2016.01)

(52) U.S. Cl.
CPC ............ *A23K 40/35* (2016.05); *A23K 20/158* (2016.05); *A23K 50/15* (2016.05)

(58) Field of Classification Search
CPC ........ A23K 40/35; A23K 50/10; A23K 50/15; A23K 20/158; A61P 3/00; A61P 43/00
(Continued)

(56) References Cited

U.S. PATENT DOCUMENTS

| 4,948,589 A | 8/1990 | Iijima et al. |
| 2007/0151480 A1 | 7/2007 | Bloom et al. |

(Continued)

FOREIGN PATENT DOCUMENTS

| GB | 1 493 425 A | 11/1977 |
| WO | WO 2012/159186 A1 | 11/2012 |
| WO | WO 2015/197719 A1 | 12/2015 |

OTHER PUBLICATIONS

Holder, Vaughn B., "The Effects of Slow Release Urea on Nitrogen Metabolism in Cattle" (2012). https://uknowledge.uky.edu/animalsci_etds/6. accessed Jul. 30, 2022. (Year: 2012).*

(Continued)

*Primary Examiner* — Subbalakshmi Prakash
(74) *Attorney, Agent, or Firm* — Oblon, McClelland, Maier & Neustadt, L.L.P.

(57) ABSTRACT

Disclosed are compositions comprising NPN compound coated with a bypass agent allowing ruminal bypass of the composition and a method for increasing fiber digestibility, a method for increasing feed intake, a method for increasing somatic growth, a method for increasing milk production, a method for reducing N excretion in a ruminant, a method for improving rumen pH stability in a ruminant, a method for preventing or reducing ammonia toxicity in the rumen. The compositions and methods of the invention are particularly (Continued)

Sealing of cracks by drum coating suitable for ruminants that are held in harsh climates and/or at remote locations from a farm.

18 Claims, 17 Drawing Sheets

(58) Field of Classification Search
USPC .......................................................... 426/635
See application file for complete search history.

(56) References Cited

U.S. PATENT DOCUMENTS

| | | | |
|---|---|---|---|
| 2010/0272852 A1* | 10/2010 | Wright | A23K 40/35 426/302 |
| 2011/0003727 A1 | 1/2011 | Bloom et al. | |
| 2012/0090367 A1* | 4/2012 | Wright | C05G 5/30 71/27 |
| 2012/0244248 A1 | 9/2012 | Wright et al. | |
| 2014/0295077 A1 | 10/2014 | Whiffen | |

OTHER PUBLICATIONS

International Search Report and Written Opinion dated Mar. 14, 2016 in PCT/EP2016/051034 filed Jan. 19, 2016.

\* cited by examiner

Fig. 1: Sealing of cracks by drum coating

Fig. 3: SEM picture of the product of example 1 (30-fold magnification)

Fig. 4: SEM picture of the product of example 1 (300-fold magnification)

Fig. 5: SEM picture of the product of comparative example 2 (30-fold magnification)

Fig. 6: SEM picture of the product of comparative example 2 (300-fold magnification)

Fig. 7: SEM picture of the product of comparative example 3 (30-fold magnification)

Fig. 8: SEM picture of the product of comparative example 3 (300-fold magnification)

Fig. 9: SEM picture of the product of comparative example 4 (30-fold magnification)

Fig. 10: SEM picture of the product of example 7 (100-fold magnification)

Fig. 11: SEM picture of the product of example 9 (30-fold magnification)

Fig. 12: SEM picture of the product of example 9 (300-fold magnification)

Fig. 13: SEM picture of the product of comparative example 11 (30-fold magnification)

Fig. 14: SEM picture of the product of comparative example 11 (300-fold magnification)

Fig. 15: SEM picture of the product of comparative example 12 (30-fold magnification)

Fig. 16: SEM picture of the product of comparative example 12 (300-fold magnification)

COMPOSITIONS FOR IMPROVING NITROGEN UTILIZATION IN A RUMINANT

FIELD OF THE INVENTION

The present invention is in the field of ruminant feeds or ruminant feed supplements that are particularly suitable for increasing feed intake, fiber digestibility, milk production, and/or somatic growth in ruminants as well as for reducing N excretion, improving rumen pH stability and/or preventing or reducing ammonia toxicity in a ruminant, particularly those held in harsh climates, such as characterized by low digestibility pastures, e.g. dry climates, hot climates, cold climates, and the like, and/or at remote locations.

BACKGROUND OF THE INVENTION

Ruminant-derived products, such as meat products (e.g. beef, sheep, lamb etc.) and dairy products (e.g. milk, cheese, butter etc.), make up a large portion of the Western diet and demand for these products is increasing. Considerable research and development efforts have been devoted to develop feeds and/or feed supplements, which may not only promote health and growth of ruminants but may also lead to improved quality and/or quantity of ruminant-derived products.

Since growth, wool and milk production are directly dependent on nitrogen availability from diet, often provided in the form of vegetable protein, supplementary protein is often used or considered to promote growth, wool and milk production in ruminants, Ruminants do not require dietary protein or amino acids per se, as proteins in the ruminant can also be synthesized by rumen microbes from nitrogen obtained from NPN sources (e.g. urea). NPN compounds (e.g. urea) are cheaper than dietary proteins. Therefore, NPN compounds have been increasingly used as an alternative or supplement to dietary proteins for promoting growth, wool and/or milk production in ruminants.

However, the use of a feed or feed supplement comprising a NPN compound (e.g. urea) is associated with ammonia toxicity in ruminants. When given in an effective amount, NPN compounds may cause ammonia toxicity. Once ingested by a ruminant, a NPN compound (e.g. urea) is rapidly converted by microbes residing in the rumen into, among other things, ammonia. With administration of an effective amount of NPN, this results in the release of a sudden peak of ammonia from the NPN source in the rumen. Ammonia toxicity ensues as the rate at which ammonia is released from urea (i.e. released as a sudden high peak) in the rumen is greater than the microbes ability to convert it to amino acids (also referred to as 'true-protein'). The excess ammonia, which is not utilized by the microbes ends up in the blood stream in high levels, which are toxic to ruminants. Symptoms of ammonia toxicity (i.e. when peripheral blood exceeds about 1 mg ammonia/100 mL of blood) include muscular twitching, ataxia, excessive salivation, tetany, bloat and respiration defects.

Significant efforts have been devoted to remedy the shortcomings associated with administration of NPN compound (e.g. urea), such as ammonia toxicity. For instance, compositions comprising a NPN compound have been developed, which allow 'delayed release' of ammonia from the NPN source in the rumen. The 'delayed release' of ammonia in the rumen is intended to dampen the sudden peak of ammonia in the rumen, which typically occurs shortly after ingestion of feed or feed supplements comprising an immediate-release NPN compound (e.g. urea). The release of ammonia, although delayed, is intended to occur in the rumen, where microorganisms can use it to produce proteins.

Delayed release of ammonia from a NPN source in the rumen is typically achieved by partially or fully coating a NPN compound with a so-called controlled release agent or coating'. Controlled release agents are characterized by their ability to delay or slow down the rate of release of ammonia from a NPN source in the rumen over time. Specifically, controlled release agents allow the release of a certain amount of ammonia from the NPN compound per unit of time, so that ammonia derived from a NPN compound is not released in bulk at once in the rumen. Various rumen by-pass agents designed for delaying or slowing down the rate of release of ammonia from NPN in the rumen over time have been developed over the years.

For instance, U.S. Pat. No. 6,231,895B1 discloses a feedstock suitable for lactating ruminants comprising a NPN compound consisting of urea encapsulated within a rumen-degradable polymeric coating. The rumen-degradable polymeric coating is used as a controlled release agent for generating ammonia under rumen incubation conditions. The feedstock is formulated to be released in the rumen at a rate that provides 6-18 mg of ammonia per decilitre of rumen fluid on a continuous daily basis. The feedstock is said to be an improvement over traditional feedstock comprising NPN, which are typically released too rapidly in the rumen, where they cause ammonia toxicity.

U.S. Pat. No. 3,015,764A1 discloses a ruminant feed consisting of a delayed and a sustained release formulation, which is intended to be released, in a delayed manner, in the rumen. The formulation comprises urea and a coating consisting of a water soluble acid or a water soluble acid neural salt form of carboxy vinyl polymer. The ruminant feed acts to provide prolonged availability of urea in the rumen, so that local microorganisms have enough time to convert it into proteins in the rumen.

WO2011116445A2 discloses a nutritional urea-based composition, which ensures the delayed release of urea in the rumen. The composition comprises urea and a coating agent consisting of hydrophobic agent such as vegetable waxes.

U.S. Pat. No. 4,035,479 discloses a delayed and sustained release formulation for rumen ingestion characterized by controlled and prolonged urea availability. The formulation comprises urea and a coating consisting of essentially water soluble acid or neutral salt form of carboxy vinyl polymer (e.g. polyacrylic acid). The authors point out that it is essential that the release of urea, although controlled and delayed, be substantially effected in the rumen, where the microflora adapted for its conversion are available.

All the above-mentioned compositions have been shown to delay the release of ammonia from a NPN source in the rumen so as to create a sustained availability of nitrogen for rumen microbes while mitigating ammonia toxicity by dampening the curve of ammonia release from the NPN source in the rumen, i.e. reducing its peak and extending its time spread. However, the above-mentioned compositions do not completely dampen the curve of ammonia release in the rumen to a flat curve. This means that, although reduced, an ammonia peak still develops in the rumen following ingestion of such NPN compound (urea). This may eventually lead to ammonia toxicity or inefficient use or waste of ammonia derived from NPN compounds by rumen microbes, particularly when NPN compounds are fed in high amounts.

Feeding increased amounts of NPN compounds would be particularly desirable for ruminants raised and/or maintained in harsh climates, as these are at a disadvantage compared to those raised and/or maintained in more favourable climates. Specifically, ruminants held in harsh climates have limited availability of nutrients, particularly proteins, from their environment. Harsh climates are characterized in that the nutritional quality of pastures growing in these areas is generally low on nutritional value (e.g., low in protein) and/or the nutritional value varies throughout the year. Additionally, the pastures in areas subjected to harsh climates are often high in fibre content, which makes them difficult to digest. Further, farms located in harsh climates are often quite remote from pastures or grass fields where ruminants or cattle animals are left to graze. This situation hampers a farmer's ability to provide ruminants or cattle animals with extra feed and/or feed supplements, such as NPN compound, on a regular basis.

As a result of the poor nutritional value and/or low digestibility of the pastures growing in harsh climates, the ruminants that feed off them do not grow and/or produce meat and/or milk optimally.

Overall, this situation leads to underperformance of ruminants or cattle held under such conditions (i.e., they have suboptimal meat production and/or milk production). This situation is undesirable for the cattle industry located in harsh climates.

Therefore, there is a need in the art for compositions comprising NPN compounds (e.g. urea) as well as methods relying on the use of compositions comprising NPN compounds, that improve or increase nitrogen utilization from a NPN compound by a ruminant, particularly for the purpose of improving or increasing fibre digestibility, somatic growth, milk production, and/or other characteristics intrinsic to ruminant biology, which are devoid of the limitations of the traditional feeds and methods using such traditional feeds, such as ammonia toxicity or inefficient use of ammonia derived from NPN compounds by rumen microbes or microorganisms.

There is also a need for compositions comprising NPN compounds (e.g., urea) as well as methods relying on the use of compositions comprising NPN compounds, which allow the inclusion of larger amounts of NPN compound in the diet of a ruminant than traditional NPN feeds, particularly for the purpose of improving or increasing fibre digestibility, somatic growth, milk production, and/or other characteristics intrinsic to ruminant biology, but which do no cause ammonia toxicity and others adverse effects or which yield better outcomes than obtained with traditional feeds.

SUMMARY OF THE INVENTION

The present invention relates to a ruminal by-pass composition suitable for ingestion by a ruminant, comprising
  a non-protein nitrogen compound, and
  a rumen by-pass agent, which allows ruminal by-pass of the non-protein nitrogen compound,
wherein the rumen by-pass agent is a coating surrounding the non-protein nitrogen compound and said coating comprises at least 90% of saturated fats.

The present invention also relates to a process of a ruminal by-pass composition according to the present invention comprising the steps of
  a) providing particles containing a non-protein nitrogen compound in a drum coater,
  b) heating the particles of step a) to a temperature in the range of from 10° C. below the melting point of the rumen by-pass agent to the melting point of the rumen by-pass agent,
  c) providing a molten rumen by-pass agent in a reservoir outside the drum coater,
  d) heating the molten rumen by-pass agent from step c) to a temperature between its melting point and 10° C. above its melting point,
  e) applying the molten rumen by-pass agent from step d) onto the particles of step b) in a rotating drum coater,
  f) maintaining the temperature of the particle bed at the temperature of the melting point of the rumen by-pass agent or slightly below the melting point of the rumen by-pass agent, and
  g) cooling the composition obtained from step f) or allowing the composition obtained from step f) to cool down.

GENERAL DEFINITIONS

In the present description and examples, a number of terms are used. In order to provide a clear and consistent understanding of the specification and claims, including the scope to be given to such terms, the following definitions are provided. Unless otherwise defined herein, all technical and scientific terms used have the meaning commonly understood by one of ordinary skill in the art to which this invention belongs. The disclosures of all publications, patent applications, patents and other references are incorporated herein in their entirety by reference.

The term Increased milk production' as used herein refers to either an increase in the volume (number of litres) of milk produced or an increase in the volume (number of kilograms) of milk solids (fat, protein, sugars, particularly fat) in the milk produced. The skilled person is acquainted with methods for measuring milk production by a ruminant. In the context of the presence invention, milk production in a lactating ruminant administered with the NPN compositions as taught herein is compared to the milk production of a lactating ruminant not administered with a NPN composition as taught herein (e.g. administered with a NPN composition devoid of any coating or with a sustained release NPN composition, such as those described herein). An example of an increase milk production is for instance, when a lactating ruminant administered with the NPN compositions as taught herein display greater milk production than a lactating ruminant not administered with a NPN composition as taught herein.

The terms 'non-protein nitrogen', 'NPN', 'non-protein nitrogen compound' or 'NPN compound' as used herein refer to any nitrogenous species, which is not a protein, peptide, amino acid or mixture thereof, that provides bio-available nitrogen to an animal's gut microbiota upon introduction into the intestinal tract of the animal. A non-limiting example of a source of NPN for animal feed is urea, which produces ammonia or ammonium ion to the animal during digestion. Other non-limiting sources of NPN include, for example, biuret, ammonium acetate, ammonium sulfate, ammonium butyrate, methylene urea, and an ammonium salt of an amino acid. Additional sources include, for example, acetamide, ammonia, butryamide, dicyanoamide, formamide, ethylene urea, isobutanol diurea, lactosyl urea, propionamide, uric acid and urea phosphate. Suitable ammonium salts also include, for example, the acetate, bicarbonate, carbamate, carbonate, chloride, citrate, formate, furmerate, lactate, maleate, phosphate, polyphosphate, propionate, succinate and sulfate ammonium salts, or any other suitable ammonium salt.

The term 'ruminants' or 'ruminant animals' as used herein refers to mammals, both males and females, that are able to acquire nutrients from plant-based food through fermentation in a specialized stomach chamber prior to digestion, principally through bacterial actions. The process typically requires regurgitation of fermented ingesta (known as cud), and chewing it again. The process of rechewing the cud to further break down plant matter and stimulate digestion is called 'rumination'. The primary difference between ruminant animals and non-ruminant animals is that ruminant animals have a four-chambered stomach.

In the rumen most of the fermentation of feed material takes place. The rumen is populated by several phyla of microorganisms, which result in fermentation of feedstuffs. In the reticulum similar fermentation functions are carried out. The rumen and reticulum are often refer to as the 'reticulorumen', which essentially consists of a 'fermentation chamber' containing micro-organisms which convert plant carbohydrate to volatile fatty acids (mainly acetate, propionate and butyrate), lactate, carbon dioxide, methane and hydrogen. The rumen-reticulum is the first compartment and functions as a fermentation chamber where feedstuff is broken down by microorganisms to short chain fatty acids that are used as an energy source by the animal itself. As a fermentation chamber, the rumen works like a reservoir of feed, with continuous outflow per hour of fermented material, also referred to as 'passage rate'. The term 'passage rate' as used herein is defined as the rate at which rumen-reticulum digesta leaves a compartment of the gut (e.g. rumen) and is expressed as the percentage of the compartment content flowing to the next compartment (e.g. abomasum) per hour (%/h). The rate of passage from the rumen-reticulum to the abomasum is much lower than from the abomasum to the remaining intestinal tract. Typically, the rate of passage between the rumen-reticulum and the abomasum is about 4-6% per hour, while the rate of passage between the abomasum and the intestine is about 50% per hour.

The omasum serves as a gateway for the abomasum allowing absorption of volatile fatty acids and water to reduce the volume of digesta reaching the abomasum. The abomasum is often referred to as the direct equivalent of the monogastric stomach, and is often called the 'true stomach' due to its ability to digest and degrade feed materials in an acidic and enzymatic environment. Material digested in the abomasum (also called digesta) transits into the small intestine, where the further digestion and absorption of nutrients occurs. Non-limiting examples of ruminants include bovine animals such as dairy cattle, beef cattle, sheep, goats, buffalo, moose, elks, bison, giraffes, yak, deer, antelopes, and the like.

The term 'bovine animals' or 'bovine' as used herein refers to a variety of bovine animals including cows, bulls (beef), steers, stags, heifers, calves, oxen, and the like. In the present invention, bovine animals include both domestic and wild bovine animals and male and female bovine animals (particularly lactating females). Bovine animals may be of the genus Bos, e.g., the species Bos taurus, Bos indicus, or the like.

The term 'ovine animals' or 'ovine' as used herein refers to animals belonging to the Ovis genus of mammals, which is part of the goat-antelope subfamily of the ruminant family Bovidae. Non-limiting examples of ovine animals include sheep, mouflon, urial, and the like. In the present invention, ovine animals include both domestic and wild ovine animals and male and female ovine animals (particularly lactating females).

The term 'caprine animals' or 'caprine' as used herein refers to animals belonging to the Capra genus of mammals, which is part of the Caprinae subfamily of the ruminant family Bovidae. Non-limiting examples of caprine animals include goat, ibex, markhor and the like. In the present invention, caprine animals include both domestic and wild caprine animals and male and female caprine animals (particularly lactating females).

The term 'lactating ruminant' as used herein refers to a ruminant animal which is capable of producing milk post-parturition.

The term 'dairy ruminant' as used herein refers to a ruminant animal, whose milk is used for commercial purposes.

The term 'cattle' or 'cattle animals' as used herein refers to a group of animals living in a herd, either domesticated or wild. Non-limiting examples of cattle animal include domesticated or wild grazing ungulates, such as cows, beef (bulls), steers, stags, heifers, oxen, sheep, goat and the like. Cattle are typically raised as livestock for meat (e.g. beef and veal), as dairy animals for milk and other dairy products (e.g. butter, cheese), and as draft animals (e.g. oxen or bullocks, for pulling carts, plows and the like). Other products derived from cattle include leather, wool, and dung for manure or fuel, and the like.

The term 'beef cattle' as used herein refers to cattle raised for meat production, as distinguished from dairy cattle animals, which are used for milk production. The meat of adult beef cattle is known as beef. The meat of juvenile beef cattle is known as veal. While the principal use of beef cattle is meat production, other uses include leather and other products.

The term 'ruminal bypass non-protein nitrogen (NPN) composition' as used herein refers to a non-protein nitrogen (NPN) composition, which substantially escapes hydrolysis, digestion and/or fermentation (i.e. at least 50%, preferably 80% and more) in the rumen and substantially bypasses the rumen, in a substantially intact form (i.e. at least 50%, preferably 80% and more intact or not digested), into the post-rumen part of the digestive system, such as the abomasum and the lower intestine (e.g. small intestine). The ruminal bypass non-protein nitrogen (NPN) composition may then be metabolized, released and/or absorbed by the post-rumen portions of the ruminant digestive system, such as the abomasum and the lower intestine (e.g. small intestine).

The term 'substantially bypass the rumen' as used herein means that at least 50%, preferably 55%, preferably 60%, preferably 65%, preferably 70%, preferably 75%, preferably 80%, preferably 85%, preferably 90%, more preferably 95% or more, of the NPN compound administered in the form of ruminal bypass NPN composition leaves the rumen in undigested form or non-hydrolysed form. Also encompassed by the term 'substantially bypass the rumen' is a NPN composition that, once having bypassed the rumen, yields a ruminal bypass fraction of NPN compound of at least 50%, preferably 55%, preferably 60%, preferably 65%, preferably 70%, preferably 75%, preferably 80%, preferably 85%, preferably 90%, more preferably 95% or more. Also encompassed by the term 'substantially bypass the rumen' is a NPN composition having a rate of release in the rumen or ruminal release rate of NPN compound of less than 5% per hour, preferably 4% per hour, preferably 3% per hour, preferably 2% per hour, more preferably 1% per hour or less.

The term 'ruminal bypass fraction' as used herein refers to the fraction or amount of NPN compound (e.g. urea), relative to the total amount of NPN compound (e.g., urea) comprised in the composition as taught herein prior to ingestion by a ruminant, that bypasses the rumen.

The term 'rate of release of NPN in the rumen' or 'ruminal release rate' as used herein refers to the amount of NPN compound (e.g. urea), expressed in weight % of the total amount of NPN compound (e.g. urea) comprised in the composition as taught herein prior to ingestion by a ruminant, that is released (i.e. digested) in the rumen per hour.

In order to make a NPN composition bypass the rumen of a ruminant one may use a so-called 'bypass agent' or 'ruminal bypass agent'. Typically, compositions comprising a core of NPN compound (e.g. urea) are coated with a 'bypass agent' or embedded within the 'bypass agent' so as to form a matrix.

The 'ruminal bypass fraction' and 'ruminal release rate' of any given NPN composition coated with a 'bypass agent' or embedded within a 'bypass agent' can be determined or measured using any methods suitable for this purpose known in the art. The skilled person is well-acquainted with methods for measuring or determining the 'ruminal bypass fraction' and 'ruminal release rate' of a NPN composition. For instance, the in sacco method (also referred to in the art as 'the nylon or polyester bag') as taught herein in the example section may be used.

The term 'sustained release agent' as taught herein refers to agents or compositions that have the ability to delay or slow down the rate of release of ammonia from a NPN source, in the rumen over time. Typically, sustained release agents are designed to allow the release of a certain amount of ammonia from a NPN compound (e.g. urea) per unit of time, so that ammonia from the NPN source (e.g. urea) is not completely released at once in the rumen. Various sustained release agents designed for delaying or slowing down the rate of release of ammonia from NPN in the rumen over time have been developed over the years. Non-limiting examples of sustained release agent include those described in U.S. Pat. Nos. 6,231,895, 3,015,764A1, WO2011116445, U.S. Pat. No. 4,035,479, and others. In the present invention, any NPN compound comprising compositions coated with a sustained release agent that delays or slows down the rate of release of ammonia from a NPN source, in the rumen over time, are considered as 'sustained release NPN compositions'.

The term 'bypass agent' or 'ruminal bypass agent' as used herein refers to agents or compositions that have the ability to substantially resist degradation, hydrolysis or digestion in the rumen over time. A 'bypass agent' or 'ruminal bypass agent' can substantially resist degradation, hydrolysis or digestion in the rumen over time because they are substantially non-degradable under conditions (e.g. pH, temperature etc) that prevail in the rumen and/or cannot be degraded by the microorganisms living in the rumen (e.g. because they do not produce the proper enzymes for substantially degrading the bypass agent). Typically, 'bypass agents' or 'ruminal bypass agents' are used to substantially prevent the release of an active ingredient (e.g. drug, antibiotics, vitamins etc) in the rumen, where it would be disadvantageous or wasted or destroyed. Instead, they ensure release of the active ingredient in the post-rumen part of the digestive system, i.e. the abomasum and subsequent part of the intestine (e.g. small intestine), where it can exert its activity for the ruminant.

As used in the context of the present invention, the ruminal bypass agent is suitable for ingestion by a ruminant. This means that the bypass agent should not cause any substantial adverse effects on the health of the ruminant.

One important aspect to consider with respect to the choice of a suitable 'bypass agent' or 'ruminal bypass agent' suitable for use in the present invention, is the ability of the bypass agent to substantially resist degradation in the rumen during the residence time in the rumen. For most ruminants (e.g. cow, sheep, etc), the average residence time within the is about 20 hours. Therefore, preferably the 'bypass agent' or 'ruminal bypass agent' of the invention is capable of substantially withstanding degradation by the digestive enzymes of rumen microflora for substantially the entire rumen residence time of about 20 hours. Preferably, the NPN (e.g., more than 50%, preferably 60%, preferably 70%, preferably 80%, more preferably 90% or more of the original amount prior to ingestion) can be released in the abomasum and subsequent parts of the digestive system. In contrast, sustained release agents or compositions that delay or slow down the rate of release of ammonia from a NPN source, in the rumen over time, for instance sustained release agents such as US4035470, provide rather limited protection against degradation in the rumen over the residence time in the rumen (depending on the diet, the residence time may vary between 14-40 hours, but is on average about 20 hours for prills).

In the present invention, NPN compositions coated, preferably fully coated, with a suitable bypass agent, such as those taught herein are considered 'ruminal bypass NPN compositions'.

The terms 'harsh environment(s)' or 'harsh climate(s)' as used herein refer to hot and/or dry and/or cold and/or windy climates, and any mixture thereof. Non-limiting examples of harsh climates include climates such as found in Brazil, Australia, South Asia, Africa, and the like.

In the present invention, the international Köppen classification system is used to classify climates based on the concept that native vegetation is the best expression of climate. More specifically, the international Köppen classification system takes into account vegetation distribution as well as average annual and monthly temperatures and precipitation, and the seasonality of precipitation. The skilled person is well-acquainted with the international Köppen classification system.

In the present invention, non-limiting examples of climates that may qualify as harsh climates include the so-called Aw climate (tropical wet and dry or savanna climate) and Am climate (tropical monsoon). Aw and Am climates are most commonly found in South America, Central America, Africa, India, South Asia, and north of Australia. Aw climates have a pronounced dry season, which occurs in winter with the driest month having precipitation less than 60 mm and less than $\frac{1}{25}$ of the total annual precipitation. Am climates result from the monsoon winds, which change direction according to seasons. Am climates are also characterized by a wet and a dry season, and in the driest month of the year, rainfall is less than 60 mm, but more than $\frac{1}{25}$ the total annual precipitation.

The term 'fiber digestibility' as used herein refers to the extent or ease with which fibers are digested by an organism such as a ruminant. The extent or ease at which dietary fibers (which are derived from plant fibers) are digested depends on many factors including diet factors (e.g. quality of the dietary fibres such as grass) and internal body factors such as microbial population, degrading enzymes, ruminal pH, energy levels, and others. Ruminant diet is largely based on plant sources, which are rich in fibers. Plant fibers have three major components: cellulose, hemicellulose, and lignin.

Cellulose and hemicellulose are to some extent digestible by ruminants. Lignin is indigestible and thus cannot be used by ruminants for energy. Ruminants themselves do not produce the enzymes necessary to break down fibers. Instead they rely on microorganisms, which produce enzymes to break down dietary fibers. The only two places in the digestive tract where any appreciable fiber digestion occurs are in the rumen and in the large intestine, with most of the fibre being digested in the rumen.

The skilled person is well-acquainted with methods for determining fiber digestibility in a ruminant. For instance, fiber digestibility may be assessed using the method described in Casali et al., R. Bras. Zootec., Vol 37: 335-342 (2008). Fiber digestibility may, for example, be determined based on the apparent indigestibility of feed as a starting point. In this method, faecal excretion is the basic parameter of indigestibility of a feed or diet, because it represents the portion of ingested feed, which was not digested during passage through the gastrointestinal tract of the ruminant. Faecal mass can be estimated with the use of well-known markers.

The term 'dry matter' (abbreviated as (DM)) as used herein refers to the moisture-free content of a given sample. The skilled person is well-acquainted with methods for measuring the dry matter content of a given sample.

The term 'dry matter digestibility' (abbreviated as (DMD)) as used herein refers to the proportion of the digested forage or feed.

The term 'crude protein' (abbreviated as (CP)) as used herein refers to a measure of the nitrogen content of a feedstuff, including both true protein and non-protein nitrogen. The term 'neutral detergent fiber' (abbreviated as (NDF)) as used herein refers to a measure of the structural components of a plant, specifically cell wall (i.e. lignin, hemicellulose and cellulose), but not pectin. Typically, NDF measurement involves the use of a neutral detergent solution is used to dissolve the easily digested pectins and plant cell contents (proteins, sugars, and lipids), leaving structural components of a plant, i.e. fibrous residue that is primarily cell wall components of plants (cellulose, hemicellulose, and lignin). NDF represents the most common measure of fiber used for animal feed analysis, but it does not represent a unique class of chemical compounds.

The term 'acid detergent fiber' (abbreviated as (ADF)) as used herein refers to a measure of the least digestible plant components, including cellulose and lignin.

The term 'ether extract' (abbreviated as (EE)) as used herein refers to the crude fat content of a feedstuff.

The term 'ammonia toxicity' (having the formula $NH_3$) as used herein refers to a situation where ammonia levels in the blood exceed a certain ammonia threshold, i.e. when peripheral blood exceeds about 1 mg ammonia per 100 mL of blood), which in turn causes toxicity symptoms in a ruminant, e.g. neurological symptoms. Nitrogen sources in the rumen are commonly divided into two categories; degradable crude protein (RDP) and non-protein nitrogen (NPN). Both RDP and NPN are hydrolyzed and utilized by rumen microbes. RDP is rapidly degraded into peptides and amino acids. Peptides can then be converted to amino acids or converted directly to microbial protein. Amino acids can be used directly by microorganisms for protein synthesis or can be further broken down through deamination to produce carbon skeletons and NPN compounds, such as ammonia or urea (Namkim, 2010). Ammonia derived from NPN compounds (e.g. urea) can also be used by microorganisms in the rumen as a source of nitrogen. Overall, nitrogen in the rumen is known to promote the fermentation of carbohydrates and to improve fibre digestibility and microbial protein synthesis.

Under normal conditions (i.e. standard ruminant diet), the rumen ammonia pool derived from the diet is typically very small (estimated to be around 5-20 mg/dL of ruminal fluid) and turns over rapidly, i.e. the ammonia not utilized by rumen microbes will normally be absorbed by the reticulo-rumen wall to ultimately reach the liver, where it will be converted into urea. A portion of rumen ammonia may also be incorporated into the microbial protein. Some of the ammonia produced in the rumen may also be absorbed in the abomasum or subsequent parts of the digestive tract (e.g. small intestine) but ultimately, ammonia will be sent to the liver, where it will be converted to urea. Excess of rumen ammonia post-metabolism would be discarded in the urine after conversion to urea in the liver. In maintaining the ammonia level in the rumen, urea produced by the liver can return to the rumen by diffusion through the rumen wall and saliva.

However, the use of NPN compound, particularly when fed in high amounts (e.g. more than about 1% of the total dry weight of feed per day) may disrupt the ruminal ammonia metabolism prevailing under normal condition as described above, and cause ammonia toxicity. At pH prevailing in the rumen, NPN compounds (e.g. urea) diffuse very quickly in the rumen, where ammonia levels suddenly reach a high peak. Ammonia toxicity typically occurs because the rate at which ammonia is released from urea (i.e. released as a sudden high peak) in the rumen is greater than the microbes' ability to utilize it or to convert it to amino acids. The excess of ammonia in the rumen is then sent to the blood stream and liver while some part is excreted as urine. Further, excessive ammonia (e.g. when blood levels are very high) may bypass the liver and go from the blood directly to the brain (via the lymphatic system).

Ammonia toxicity is typically reflected as reduced growth, reduced lactation, reduced feed intake, muscular twitching, ataxia, excessive salivation, tetany, bloating, respiration defects and others.

The term 'nitrogen recycling' as used herein refers to the ability that ruminants have to recycle systemic nitrogen back to the rumen. Nitrogen recycling typically occurs via blood and gut lumen exchanges of urea and ammonia. Nitrogen can re-enter the digestive tract, mainly through the rumen wall, where it can be absorbed again or be re-used for microbial protein synthesis and finally anabolic purposes. Nitrogen recycling thus allows conversion of catabolic nitrogen into anabolic nitrogen. This allows nitrogen to remain longer in the body and increases the chance to utilize dietary nitrogen sources efficiently or to the fullest. Nitrogen recycling is maximized or enhanced when urea blood levels are high. In addition, products of ruminal fermentation (i.e., volatile fatty acids and $CO_2$) also contribute to the influx of urea from the blood stream into the rumen.

The term 'rumen pH stability' as used herein refers to substantially constant pH conditions, typically ranging from pH 5.5 to pH 6.8, with fibre-digesting bacteria thriving best at pH 6.0-6.8 and starch-digesting bacteria at 5.5-6.0. Typically, the best balance of fibre and starch digestion occurs at a rumen pH of around 6.0. Thus, the rumen may be regarded as a fermentation chamber only functioning optimally within narrow physical/chemical limits. Small changes, e.g. of pH, will easily disturb the fine symbiotical balance between various kinds of microorganisms, almost all of which have specific functions in the complex fermentation processes in the rumen. This overall will adversely affect (decrease)

digestion of fibres, which in turn will affect (lower) appetite and food intake. Factors affecting rumen pH and fermentation efficiency include high forage diets, high feed intakes, diet rich in starch, diet rich in NPN, and others. The release of NPN compound into the rumen typically increases ruminal pH to values above pH 6.7. At such pH levels, rumen fermentation is impaired.

Rumen pH, at any given point in time, can be measured or determined by any methods suitable for achieving this goal. The skilled person is well-acquainted with methods suitable to measure or determine ruminal pH. For instance, rumen pH can be measured as taught herein in the example section.

The term 'nitrogen excretion' as used herein refers to nitrogen found or measured in faeces and urine. The skilled person is capable of determining nitrogen excretion using known methods. One such method is described herein in the examples section.

The term 'nitrogen utilization' or 'nitrogen retention' as used herein refers to the proportion of the nitrogen ingested that is retained in the ruminant's body. In the present invention nitrogen utilization may be determined by any suitable method known in the art, for instance by measuring the nitrogen intake and nitrogen excretion in faeces and urine. A non-limiting example of a method for determining nitrogen utilization is described by Hoffman et al. (J. Dairy Sci. 2001. Vol. 84:843-847).

The term 'somatic growth' as used herein refers to growth of the body in terms of height and/or weight. Somatic growth is also understood to refer to a positive change in size (i.e. gain in height and/or weight), for example, over a period of time. Somatic growth may occur as a stage of development or maturation or during adulthood. In the present invention, somatic growth is determined by recording the body weight of a ruminant before and after treatment with the composition as taught herein (i.e. composition comprising a NPN compound (e.g. urea) and a rumen by-pass agent). Specifically, somatic growth is determined by subtracting the body weight measured after administering said composition from the body weight measured before administering said composition as shown in the following formula:

Somatic growth=[body weight before onset of treatment with the composition as taught herein]–[body weight after termination of the treatment with the composition as taught herein]).

For instance, an increase in body weight in response to treatment with said composition indicates an increase in somatic growth while a decrease or no change in body weight indicates a decreased or unchanged somatic growth, respectively.

The term 'feed intake' as used herein refers to the amount (volume or weight) of feed voluntarily ingested by a ruminant in a certain period of time, for instance in one day. In the present invention, feed intake may be determined by weighting and recording, on a daily basis, the amount of feed provided at a time point 0 (for instance, at the beginning of the day around 8 AM) and the amount of leftover feed is typically measured 24 hours later (for instance, around 8 AM on the next day). Feed intake is calculated by subtracting the amount of feed not eaten at the end of the day from the amount of feed provided to a ruminant at the beginning of the day (i.e. feed intake=[amount of feed provided at the beginning of the day]–[amount of feed left intact (i.e. not eaten) at the end of the day]).

The term 'about', as used herein indicates a range of normal tolerance in the art, for example within 2 standard deviations of the mean. The term "about" can be understood as encompassing values that deviate at most 10%, 9%, 8%, 7%, 6%, 5%, 4%, 3%, 2%, 1%, 0.5%, 0.1%, 0.05%, or 0.01% of the indicated value.

The terms 'comprising' or 'to comprise' and their conjugations, as used herein, refer to a situation wherein said terms are used in their non-limiting sense to mean that items following the word are included, but items not specifically mentioned are not excluded. It also encompasses the more limiting verbs 'to consist essentially of' and 'to consist of'.

Reference to an element by the indefinite article 'a' or 'an' does not exclude the possibility that more than one of the elements is present, unless the context clearly requires that there be one and only one of the elements. The indefinite article 'a' or 'an' thus usually means 'at least one'.

The terms 'to increase', 'to decrease' or 'to improve', as taught herein, refer to the ability to significantly increase or significantly decrease or significantly improve an outcome. Generally, a parameter is increased or decreased or improved when it is at least 5%, such as 10%, 15%, 20%, 25%, 30%, 35%, 40%, 45%, 50% higher or lower or improved, respectively, than the corresponding value in a control. In the context of the present invention, the control may be a ruminant which did not receive an NPN composition as taught herein. Alternatively or additionally, the control may be a ruminant which received NPN compound in a composition lacking a ruminal bypass agent allowing at least 50% bypass of the rumen or received a sustained release NPN composition, which does not allow at least 50% bypass of the rumen. When comparing whether or not any of the parameters taught herein are increased or decreased or improved, the test ruminant and the control are preferably of the same genus and/or species.

DETAILED DESCRIPTION OF THE INVENTION

The present inventors surprisingly found that administering to a ruminant, an NPN composition as taught herein, which allows a ruminal bypass fraction of at least 50% (preferably 80% or more), and which as a rate of release of NPN in the rumen of less than 5% per hour, led to various advantageous effects including: 1) increased or improved feed intake, 2) increased or improved fibre digestibility, 3) increased or improved somatic growth, 4) increased or improved milk production, 5) reduced N excretion in urine, 6) improved rumen pH stability, and 7) prevention or reduction of ammonia toxicity in said ruminant, in comparison to a ruminant administered with a NPN composition, which does not have the characteristics as described above (e.g. non-protected urea and/or sustained release NPN compositions).

Without being bound to any theories, it is believed that the above-mentioned advantages are achieved as a consequence of the pattern of ammonia release and absorption of ammonia in the abomasum and subsequent parts of the digestive system afforded by the NPN compositions taught herein, in conjunction with the endogenous ability of ruminants to recycle systemic nitrogen back to the rumen.

With a ruminal bypass fraction of NPN of at least 50% (preferably 80% or more), most of the NPN is released and absorbed in the abomasum and subsequent parts of the digestive system (e.g. small intestine), and not in the rumen. This represents a paradigm shift in the field of ruminant nutrition. At the time of filing of the present application, the prevailing school of thoughts, with respect to administering a NPN compound to a ruminant, was to have NPN-derived ammonia predominantly released (>70%), preferably in a sustained manner, in the rumen. It was thought that it was important that NPN compound (e.g. urea) should be substantially released in the rumen over time, where the microorganisms adapted for its conversion are available.

In contrast, the present inventors found that when the release of NPN compound (e.g. urea) is substantially effected (i.e. at least 50%, preferably 80% or more) in the abomasum and subsequent parts of the digestive system instead of the rumen, this is more advantageous to the ruminant.

The release of substances from the rumen to the lower sections of the ruminant gastrointestinal tract follows a very slow logarithmic pattern due to the passage rate of digesta and fluid between the rumen-reticulum and abomasum. Hence, small fractions of rumen contents leave the rumen every hour creating a slowly decreasing post-ruminal supply of any rumen-resistant compound brought into the rumen.

In the case of the ruminal bypass NPN composition as taught herein, the effect is a small but steady NPN supply to the bloodstream of the ruminant, which can efficiently be handled by the ruminant's body. A portion of the NPN will re-enter the rumen by means of nitrogen recycling, where nitrogen is utilized by the rumen microbes for protein production. As a result, no substantial ammonia NPN peak is generated, over time, neither in the rumen nor in the blood, thus increasing the efficacy of nitrogen utilization (i.e. microorganisms in the rumen make use of substantially all the nitrogen to produce proteins) as well as reducing nitrogen excretion (i.e. which serves as an index of increased nitrogen utilization and digestibility).

Because ruminants have the ability to recycle systemic nitrogen back to the rumen, a steady flow of small amount of nitrogen reaches the rumen per hour throughout the day (i.e. 24 hour period) as a result of one feeding event. In this way, the microorganisms in the rumen can convert substantially all the nitrogen into more amino acid in a real-time manner, without being subjected to an overload of NPN (i.e. meaning that substantially all the NPN is utilized by the microorganism over time, with no substantial excretion of nitrogen or overflow of nitrogen to the blood stream). As a result, the NPN is efficiently used and no NPN is lost. Overall, this enhances or improves the fermentative function of the rumen having diets where nitrogen is limiting for carbohydrate digestion, e.g. ruminant held in harsh environmental conditions or exposed to or fed grass having poor nutritional quality. In turn, fibre digestibility in the rumen and food intake are increased, pH stability in the rumen is promoted, nitrogen excretion in the urine is reduced (i.e. meaning that nitrogen digestibility is increased) and protein production is increased, which proteins are directly available to the ruminant for milk production, wool, somatic growth, and other processes.

The inventors also found that because no toxicity was associated with the compositions taught herein, more NPN (i.e. more than 1% of the total dry weight of feed) can be included in the diet without causing toxicity, e.g. from 1% up to 100% of the total dry weight of feed) compared to amounts usually given with traditional NPN compositions, i.e. amount below or not exceeding 1% of the total dry weight of feed). The increased threshold of inclusion of NPN in ruminant diets represent an economic advantage in ruminant nutrition, while at the same time allowing for more sustainable milk, wool and/or meat production through a reduction in the use of true protein sources.

Ruminal Bypass Compositions

In a first aspect, the present invention relates to a ruminal by-pass composition suitable for ingestion by a ruminant, comprising
 a non-protein nitrogen compound, and
 a rumen by-pass agent, which allows ruminal by-pass of the non-protein nitrogen compound,
wherein the rumen by-pass agent is a coating surrounding the non-protein nitrogen compound and said coating comprises at least 90% of saturated fats.

The term 'a ruminal bypass non-protein nitrogen (NPN) composition suitable for ingestion by a ruminant' as used herein, refers to a composition that is not toxic or which does not cause substantial harm to the ruminant or does not substantially affect the well-being of the ruminant. The skilled person knows how to determine whether a given NPN composition is suitable for ingestion by a ruminant.

In an embodiment, the NPN composition as taught herein is devoid of sulfur and/or phosphate containing urea and/or any sulfur or phosphate derivatives of urea and/or sulphur or phosphate related compounds, for example sulfur-coated urea because sulfur-coated urea has a more tight coating structure and thus, has a very slow release rate of urea, i.e. over months, e.g. one season.

In an embodiment, the NPN composition as taught herein has a ruminal bypass fraction of NPN of at least 50%, preferably 60%, preferably 70%, preferably 80%, more preferably 90% and more. This means that, compared to the total amount of NPN comprised in the composition prior ingestion by a ruminant, at least 50% of said total amount of NPN has bypassed the rumen, in an undigested form, after about 20 hours post ingestion.

In principle, the coating surrounding the core of NPN may be any coating or composition capable of providing a rate of release of NPN in the rumen of less than 5 wt. % per hour, preferably less than 4 wt. % per hour, preferably less than 3 wt. % per hour, preferably less than 2% per hour, more preferably less than 1% per hour and/or has a ruminal bypass fraction of NPN of at least 50%, preferably 60%, preferably 70%, preferably 80%, more preferably 90% and more, preferably the coating has or maintains the properties described above during the entire residence time in the rumen of the NPN composition coated with said coating, i.e. about 20 hours.

However, it was found that not all available coating materials guarantee to achieve this goal. Further, it is advantageous to use a coating of natural source such vegetable fats since these materials allow the production of digestible coatings for animals, in particular for ruminants, and also provide a nutritional value as an additional benefit for the animal. In addition the new coating method developed herein also allows to by-pass protect the urea with relatively low levels of fat, e.g. 20 wt.-% fat coating and 80 wt.-% urea.

By comparison, the prior art teaches to use polymers and in particular indigestible artificial polymers without any nutritional benefit for the animals for protective coating of biologically active substances.

For instance, U.S. Pat. No. 3,619,200 describes a feed or feed supplement that has been rendered resistant to breakdown within the rumen by application of a protective coating consisting of synthetic polymers or copolymers of basic acrylic or basic vinyl monomers (e.g. (2-vinylpyridine), poly (4-vinylpyridine), and poly (N-vinylpyrrolidone), poly (tert-butylaminoethyl methacrylate), or co-polymers thereof).

U.S. Pat. No. 3,880,990 discloses an orally administrable ruminant composition comprising a medicinal substance encapsulated or embedded in a physiologically acceptable basic polymer. Suitable basic polymers include: imidamine polymers ("rumen lacquer", see Belgian Pat. No 703820) or copolymers of methacrylic acid and basic methacrylic acid amides (e.g. a copolymer of 1-amino-3-dimethyl-aminopropyl-methacrylic acid amide and methacrylic acid methyl ester), polyacrylic acid derivatives with basic groups (e.g. Eudragit® E from Evonik, a polyacrylic acid derivative, in which the carboxyl groups are wholly or partially esterified with dimethylaminoethanol or similar aminoalcohols), aminocellulose derivatives (e.g. benzylamino-methylcellulose, diethylamino-methylcellulose, 1-piperidyl-ethyl-hydroxyethylcellulose, and benzylamino-ethylhydroxy-ethylcellulose), aminoacid esters of cellulose or cellulose derivatives (e.g. N,N-diethylglycinemethylcellulose, acetylcellulose-p-amino-benzoate, ethylhydroxyethylcellulose-p-aminobenzoate and cellulose acetate-diethylaminoacetate), polyvinylamines (e.g. N-benzyl-polyvinylamine, N-phenyl-polyvinylamine and piperidino-polyvinylamine, copolymers of vinylamine and vinyl acetate), polyvinylaminoacetals (e.g. polyvinyl-N,N-diethylaminoacetacetal, polyvinyl-N-benzylaminoacetacetal, polyvinylpiperidinoacetacetal, copolymers of vinyl-N, N-diethylamino-acetacetal or vinyl-N-dodecylaminoacetacetal or vinylpiperidino-acetacetal and vinyl acetate), poly(vinylpyridine) derivatives (e.g. poly(2-vinyl-pyridine), poly(4-vinylpyridine), poly(2-methyl-5-vinylpyridine) and poly(2-vinyl-5-ethylpyridine), and copolymers of these vinyl compounds with each other or with other vinyl compounds or with acrylic or methacrylic copolymers), saccharide-p-aminobenzoate (e.g. sucrose-p-aminobenzoate, lactose-p-aminobenzoate, glucose-p-aminobenzoate, fructose-p-aminobenzoate, mannitol-p-aminobenzoate and sorbitol-p-aminobenzoate), amino derivatives of sugars, polyalcohols and starch products (e.g. dodecylamino-N-glucoside, dodecylamino-N-xyloside, dodecylamino-N-lactoside, benzylamino-sucrose, benzyl-amino-dextrin and benzylamino-mannitol, polystyrenes with basis groups (e.g. dimethylaminoethylpolystyrene, acetyldimethylaminomethylpolystyrene, diethylaminomethylpolystyrene, acetyldiethylaminomethylpolystyrene, pi peridylmethylpolystyrene, N-propyl-diethanolamine-methylpolystyrene, acetylpiperidylmethylpolystyrene and acetyldiethanolaminemethylpolystyrene), and others.

WO2012054457 describes a granular feed supplement for ruminants comprising a physiologically active substance (e.g. lysine) coated with a coating consisting of one or more saturated or unsaturated (e.g. with 1 or more double bounds in cis or trans) linear aliphatic monocarboxylic acids having from 2 to 34 carbon atoms, including aliphatic monocarboxylic acids that are in free form, salts of aliphatic monocarboxylic acids, and esterified aliphatic monocarboxylic acids, such as a mono-, di-, or triglycerides, and phospholipids. Aliphatic monocarboxylic acids may be obtained from naturally occurring sources, or may be synthesized. Particular non-limiting examples include a single linear, saturated aliphatic monocarboxylic acid, such as, for example, stearic acid (c18). Another non-limiting examples include a mixture of two or more linear, saturated aliphatic monocarboxylic acids such as a mixture of stearic acid and palmitic acid in a ratio of from 20:1 to 3:1 parts of stearic acid to palmitic acid by weight. The coating material may comprise one or more aliphatic monocarboxylic acids originating from one or more sources, such as the sources described above. However, if was found that the simple and unselective use of an aliphatic monocarboxylic acid, carboxylic acid salt or of an esterified aliphatic monocarboxylic acid does not give a coating which can sufficiently protect an NPN compound from being released in the rumen.

It was found that the use of a coating material with a melting point as wide as possible, or in other words a melting range as wide as possible, allows the production of NPN comprising compounds with a slow release rate of the NPN in the rumen. In particular, the use of coating materials with a melting range as wide as possible allows the preparation of compositions which do not have any defects, such as cracks, breaks or other flaws in the protective coating layer around the NPN comprising core or which at least have only a very low number of such defects. Without wishing to be bound to a specific theory, it is believed that this effect is based on the different melting points of the components in a coating material with a wide melting range: the high-melting-point fraction of the molten coating material is solidified faster than the low-melting-point fraction of the molten coating material. Thus, the low-melting-point fraction of the molten coating material is believed to be still fluid or at least viscous for a certain time period. Possibly occurring damages in the coating layer due to cracks, breaks or failures can be immediately filled and closed by the still liquid low-melting-point fraction of the coating material during the coating process. It was found that fats or fat mixtures which contain at least 90% of different saturated fatty acids are particularly suitable to achieve this effect.

Substances with a broad melting range which are suitable for the preparation of the composition of the present invention are for example partly or completely hydrogenated fats or oils of natural source, which are composed of saturated, monounsaturated or polyunsaturated fatty acids of different chain lengths with different degree of saturation which are esterified with glycerol or contain different additives such as phospholipids, sphingolipids, cholesterol or others. Vegetable oils contain a mixture of various fats, among them saturated fats, monounsaturated fats and polyunsaturated fats. For example, palm oil contains about 46% of saturated fats, 46% of monounsaturated fats and 8% polyunsaturated fats, and soybean oil contains about 14% of saturated fats, 24% of monounsaturated fats and 62% of polyunsaturated fats. Specifically, palm oil contains for example 49% of stearic acid, 38% palmitic acid, 9% of myristic acid and other fatty acids or about 41 to about 46% of palmitic acid, about 37 to about 42% of oleic acid, about 8 to about 10% linoleic acid, about 4 to about 7% stearic acid, and about 2% or less other fatty acids, and soybean oil contains about 17 to about 31% of oleic acid, about 48 to about 59% of linoleic acid, about 2 to about 11% of linolenic acid, and other fatty acids, such as about 2 to about 11% of palmitic acid and/or 2 to 7% of stearic acid. However, natural fats or natural vegetable oils as such are not rumen stable and therefore, are not really suitable for use as ruminal bypass agents. By comparison, possible fats or oils for rumen stable product formulations are for example hydrogenated plant oils, such as palm oil, soybean oil, rapeseed oil, sunflower oil or castor oil, or hydrogenated animal fats such as beef tallow. Further coating materials can be also natural waxes such as bees wax. However, it was found that the use of hydrogenated vegetable oils as coating provides the composition with a low rate of release of urea in the rumen. It is believed that this effect is based on the wide melting range because of the different esterified fatty acids of hydrogenated vegetable oils.

In one embodiment of the present invention the coating of the compositions therefore essentially consists of hydrogenated vegetable oil.

It was further found that the use of hydrogenated palm oil gave products with a very low release rate of urea. The surface of these products appeared to have a very smooth and uniform appearance without any defects. It is believed that this is due to the wide range of melting points of the different saturated fatty acids within the hydrogenated palm oil. The hydrogenated palm oils contains a variety of fatty acids with different melting point which allows a very good self-healing of possible flaws in the coating shell.

In a preferred embodiment of the present invention the coating of the compositions therefore essentially consists of hydrogenated palm oil.

NPN comprising compositions coated with this coating have a rate of release of NPN in the rumen that is less than 5 wt. % per hour, preferably 4 wt. % per hour, preferably 3 wt. % per hour, preferably 2 wt. % per hour, more preferably 1 wt. % per hour or less and/or a ruminal bypass fraction of NPN of at least 50%, preferably 60%, preferably 70%, preferably 80%, more preferably 90% and more, preferably over substantially the entire residence time in the rumen of the NPN composition coated with said coating, e.g. 20 hours.

In one embodiment of the present invention the composition therefore has a rate of release of the non-protein nitrogen compound of less than 5 wt.-% per hour.

The use of substances with a wide melting range as coating has the further advantage that this technique does not require a fine nebulization by spraying as in most of today's process for particle coating. Rather, the use of the coating materials according to the present invention allows to drop the liquid material punctually at one single specific point or at several specific points in liquid form into the moved bed of particles. This has the further advantage that the coating material can be used as suspension together with additional components such calcium carbonate, potassium carbonate, sodium carbonate, potassium hydrogen carbonate, and sodium hydrogen carbonate, which allow the provision of coated compositions with a pH trigger. Said pH trigger helps to release the NPN compound in the abomasum in a shorter time than compounds without a pH trigger.

In one embodiment of the present invention the coating comprises a pH trigger, preferably calcium carbonate, potassium carbonate, sodium carbonate, potassium hydrogen carbonate, and sodium hydrogen carbonate.

In order to provide for the increase in feed intake, fiber digestibility, milk production and/or somatic growth, the compositions of the present invention contain an NPN compound according to the general understanding of the present invention.

In one embodiment, the NPN compound is therefore one or more compounds selected from the group consisting of urea; ammonium salts such as ammonium acetate, ammonium sulfate, ammonium butyrate and an ammonium salt of an amino acid; methylene urea, biuret, acetamide, butryamide, dicyanoamide, formamide, ethylene urea, isobutanol diurea, lactosyl urea, propionamide, uric acid and urea phosphate.

In a preferred embodiment of the present invention the the non-protein nitrogen compound is urea and/or an ammonia salt.

In an embodiment, the average particle size of the ruminal bypass NPN composition as taught herein may be in the range of about 1.0 mm to about 6 mm, or is in the range of about 1.2 mm to about 5 mm, or is in the range of about 1.2 mm to about 4 mm, or is in the range of about 1.2 mm to about 3 mm, or is in the range of about 1.2 mm to about 2.8 mm, or in the range of about 1.4 mm to about 2.6 mm, or in the range of about 1.6 mm to about 2.4 mm, or in the range of about 1.8 mm to about 2.2 mm or in the range of about 2.0 mm.

It may be advantageous that the ruminal bypass NPN composition as taught herein has an average particle size of at least about 2 mm the reducing the chance of regurgitation or vomiting by a ruminant upon ingestion.

In an embodiment, the composition as taught herein is characterized in that the ratio of NPN compound to coating is in the range of about 20:80% by weight to about 95:5% by weight, preferably from 25:75% by weight to about 85:15% by weight or from 30:70% by weight to 80:20% by weight. Preferably, the composition as taught herein contain a ratio of NPN compound to coating of 83:17 to 75:25.

In principle, the application of the coating as taught herein around an NPN or around an NPN comprising may be performed according to any suitable methods known in the art. However, it was found that the best method of providing an NPN with a coating is the drum coating. In order to achieve the aforementioned self-healing of defects in the coating layer, i.e. the filling and closing of damages in the coating layer due to cracks, breaks or failures, the still liquid fraction which is present on the particles in the moved bed of particles must be directly transferred from one particle to other particles through the direct and gentle contact of the particles. The direct contact of the particle is achieved through the continuous movement of the particles in the bed of particles. It was found that the best way of achieving this goal is to perform the coating in a rotating drum coater, in which the particles are moved at any point and at any moment and where one particle is in close contact with the highest possible number of other particles. As a consequence excess amounts of liquid fraction of the coating material, which may locally occur on the surface of a urea prill particle, are transferred though intensive contact among the particles and the adhesive forces caused by this contact from one particle to another particle with less coating on the surface. This transfer, the direct contact of the particles among each other and the permanent movement of the particles leads to the closure and sealing of defects in a coating layer. This action is also illustrated in FIG. 1: the particle with a schemed crack in the coating layer (a) gets in contact with another particles having partially molten coating material on their surface (b); by transferring some of the molten material from one particle to another during the gentle contact, the crack can be sealed and provides a rumen by-pass protected urea product (c). The permanent rolling of the particles removes irregularities on the surface of the coating on the urea prills and leads to a filling and a steady closing of holes in said coating with liquid coating material. This action is also illustrated in FIG. 2: The Figure shows that the particle with a schemed hole in the urea prill (a) gets in contact with another particles having partially molten coating material on their surface (b); by transferring some of the molten material from one particle to another during the gentle contact, the hole can be sealed and provides a rumen by-pass protected urea product (c).

It was found that these conditions and results cannot be realized with any conceivable coating technique such as a fluidized bed or drum mixing. Rather, said common techniques lead products with irregular surface and which, more importantly, do not have a closed coating around the NPN compound or the NPN comprising core. However, any defects in the coating of the products obtained by fluidized bed or drum mixing will increase the release rate of the NPN compound in the rumen, which, however, is to be avoided. This is believed to be based on the observation that fluidized bed and drum mixing fail to provide an intensive contact of the particles. Therefore, these methods fail to allow the aforementioned transfer of the still liquid coating material from one particle to another and thus, they also fail to provide for self-healing of any possible defect in the coating of the products. By comparison, the intensive contact of the particles is at maximum in a moved bed of particles. Thus, the aforementioned self-healing effects are also the best in a moved bed of particles. A moved bed of particles can be realized in a rotating drum, where the particles are moved at any moment in a very gentle way and rolled on one another. By comparison, in a fluidized bed the particles are strongly accelerated through the suspending with a swirl gas and therefore, the coating layer on a particle is exposed to extreme mechanical stress when it collides with the housing of the fluidized bed or when it collides with other particles. This leads to the formation of new breaks or cracks in the coating layer and also to the formation of fine particles. In a drum mixer the solid product is also exposed to high mechanical stress through the stirrer of the drum mixer. The stirrer creates a high pressure during the mixing and through the direct contact of the stirrer or of the housing of the mixer with the particles or through the direct contact of the particles among another the high pressure load leads to damages of the coating of the particles. As a result the products obtained by drum mixing and fluidized beds have an irregular surface appearance and are characterized by deep pressure marks (see also comparison example 6).

Therefore, in one embodiment of the present invention the coating of the NPN compound or of an NPN comprising core is performed in a drum coater.

A further advantage of the drum coating is that it allows an adjustment as precise as possible of the effective temperature of the bed of particles by controlling the fed in and the discharged heat amount by continuous regulation of the feed streams. The temperature level can be raised by increasing the mass stream of the added molten coating material or in a limited way be increasing the temperature of the fed in cooling gas. The temperature level can be decreased by lowering the mass stream of the added molten coating material or by decreasing the temperature of the cooling gas. The effective temperature of the particle bed also particularly depends on the preheating temperature of the urea prills at the start of the coating procedure. The very efficient control of the temperature in the coating process also supports the self-healing of the coating surface of particles, in particular when coating materials with a wide melting are used. It is believed that the efficient temperature in drum coating allows to specifically solidify those components of the coating material at first, which a high melting point and then the step-wise solidification of those components of the coating material which have lower melting points. The low-melting fraction of the coating material is still liquid when the high-melting fraction have just solidified and therefore, said low-melting fraction can fill and seal breaks and holes in the coating layer of a composition as taught herein.

A second aspect of the present invention is therefore, a process of a ruminal by-pass composition according to the present invention comprising the steps of
 a) providing particles containing a non-protein nitrogen compound in a drum coater,
 b) heating the particles of step a) to a temperature in the range of from 10° C. below the melting point of the rumen by-pass agent to the melting point of the rumen by-pass agent,
 c) providing a molten rumen by-pass agent in a reservoir outside the drum coater,
 d) heating the molten rumen by-pass agent from step c) to a temperature between its melting point and 10° C. above its melting point,
 e) applying the molten rumen by-pass agent from step d) onto the particles of step b) in a rotating drum coater,
 f) maintaining the temperature of the particle bed at the temperature of the melting point of the rumen by-pass agent or slightly below the melting point of the rumen by-pass agent, and
 g) cooling the composition obtained from step f) or allowing the composition obtained from step f) to cool down.

The preferred coating material for the composition as taught herein are substances with a wide melting range.

Therefore, in one embodiment of the present invention, when the rumen by-pass release agent has a melting range, the melting point of the rumen by-pass agent in step b) is the lower limit of the melting range, the melting point of the rumen by-pass agent in step d) is the upper limit of the melting range of the rumen by-pass agent, and the melting point in step f) is the melting range of the rumen by-pass agent.

In one embodiment of the present invention the rumen by-pass agent has a difference between the lower and the upper limit of the melting range of from 3° C. to 10° C.

The FIGS. 3 and 4 (SEM (scanning electron microscope) picture for the product of example 1) and the FIGS. 11 and 12 (SEM picture for the product of example 9) shows that the use of a rumen by-pass agent containing at least 90% of a hydrogenated fat, provides products with a very uniform surface without any defects such as breaks, holes or the like.

By comparison, neither drum mixing nor fluidized bed give product of comparable quality, even when the same coating materials was used, see FIGS. 5 and 6 (SEM picture for the product of comparative example 2 obtained by drum mixing) and FIGS. 7 and 8 (SEM picture for the product of comparative example 2 obtained by fluidized bed).

In one embodiment of the present invention the rumen by-pass agent contains at least 90% of a hydrogenated fat.

In one embodiment of the present invention the rumen by-pass agent essentially consists of a hydrogenated vegetable oil.

In a preferred embodiment of the present invention the rumen by-pass agent essentially consists of a hydrogenated palm oil.

In one embodiment the temperature of the molten rumen by-pass agent is between ca. 50° C. and ca. 85° C.

In a preferred embodiment the temperature of the molten rumen by-pass agent is between ca. 50° C. and ca. 65° C.

In one embodiment the temperature of the heated particles is between 40° C. and ca. 75° C.

In a preferred embodiment the temperature of the heated particles is between 42° C. and 55° C. or 42° C. to 50° C.

In one embodiment the molten rumen by-pass agent is dropped into the drum coater.

In the present invention, it may be preferable that the core of NPN be coated with one or more suitable coatings as taught herein. The NPN core may be coated with a single layer of the coating material applied in a single coating application, or the core may be coated with multiple layers of coating material, such as, for example, 2, 3, 4, 5, 6, 7, 8, 9, or more layers. Each layer surrounding the core may independently comprise the same coating material or different coating materials as taught herein. If consecutive layers of the same coating material are applied to the core as described above, the individual layers may not be distinguishable in the final product.

It may be advantageous to apply a multi-layer of coating as taught herein to prevent or conceal defects in the coating (e.g. cracks). For instance, while the liquid coating material is allowed to cool and solidify into a solid layer, defects such as micro-fissures, cracks, and pores may form in the layer. These defects can create paths for the ruminal environment to access and start degrading the core. Although any additional layers may also exhibit such defects, the defects in one layer may be offset by non-defect areas in a coating layer above or below and in direct contact with said one layer. Thus, by applying multiple layers of coating material to the core, where each layer is allowed to cool and solidify before forming the next layer, the number of defects that run continuously or create a path from the outer surface of the outermost layer to the core will decrease.

It is further understood that the number and size of the defects in a layer may vary depending on the core size, coating materials, the coating process, and the process parameters utilized for making the coated core. As such, the number of layers and the thickness of each layer necessary to obtain a desired ruminal bypass fraction of NPN and/or rate of release of NPN in the rumen, may vary depending upon the variables selected.

It is understood that the NPN compound or the NPN comprising core (e.g. urea) should be coated with a sufficient amount of coating material as taught herein to coat the core, preferably completely coat the core, and should have a particle size suitable to obtain a rumen bypass fraction of at least 50%, preferably 60%, preferably 70%, preferably 80%, more preferably 90% or more and/or a rate of release of NPN in the rumen that is less than 5% per hour, preferably less than 4% per hour, preferably less than 3% per hour, preferably less than 2% per hour, more preferably less than 1% per hour, preferably over substantially the entire residence time in the rumen of the NPN composition, e.g. 20 hours.

In an embodiment, the core comprising more than 90% wt. % NPN compound may be in the form of one or more granules of NPN or more or more prills of NPN, or may further include a matrix comprising one or more excipients such as binding substances, inert ingredients, and flow-control substances that together aid the formation of pellets of granulated or prilled NPN. It is understood that said core is suitably coated with one of more of the coatings or compositions as taught herein to produce the ruminal bypass compositions of the invention.

In an embodiment, the core comprising more than 90 wt. % of NPN compound may be made of prilled NPN, e.g. prilled urea (e.g., available at SABIC).

It is understood that, depending on the number of coating layers applied on the core comprising more than 90 wt. % NPN compound, the particle size of the NPN granules or prills as taught herein may be varied to obtain a given particle size of the finished product.

In an embodiment, the NPN compound may be selected from the group consisting of urea, ammonia, ammonium acetate, ammonium sulfate, ammonium butyrate, methylene urea, ammonium salt of an amino acid, biuret, acetamide, butryamide, creatine, creatinine, dicyanoamide, formamide, ethylene urea, isobutanol diurea, lactosyl urea, propionamide, uric acid and urea phosphate.

Suitable ammonium salts also include, for example, acetate, bicarbonate, carbamate, carbonate, chloride, citrate, formate, furmerate, lactate, maleate, phosphate, polyphosphate, propionate, succinate and sulfate ammonium salts, or any other suitable salt. In a preferred embodiment, the NPN compound may be urea and/or ammonia sulphate, more preferably urea.

In one embodiment, the composition as taught herein may comprise one or more NPN compounds selected from the group consisting of urea, biuret, ammonium acetate, ammonium sulphate, ammonium butyrate, methylene urea, ammonium salt of an amino acid, acetamide, ammonia, butryamide, dicyanoamide, formamide, ethylene urea, isobutanol diurea, lactosyl urea, propionamide, uric acid and urea phosphate. Suitable ammonium salts also include, for example, acetate, bicarbonate, carbamate, carbonate, chloride, citrate, formate, furmerate, lactate, maleate, phosphate, polyphosphate, propionate, succinate and sulphate ammonium salts, or any other suitable salt. The composition as taught herein may comprise urea and ammonium sulphate.

When preparing the composition taught herein, it may be advantageous (although not essential) to add one or more additional ingredients to the ruminal bypass agent, i.e. coating as taught herein. Representative, non-limiting examples of such ingredients include lecithin, waxes (e.g. carnauba wax, beeswax, natural waxes, synthetic waxes, paraffin waxes, and the like), fatty acid esters, magnesium carbonate, calcium carbonate, calcium phosphate, calcium pyrophosphate, calcium hydrogen phosphate hydrates, calcium hydrogen phosphate dihydrate, calcium dihydrogen pyrophosphate, magnesium pyrophosphate, magnesium hydrogen phosphate hydrates, aluminium phosphate, magnesium hydroxide, aluminium hydroxide, manganese oxide, zinc oxide, sodium hydrogen carbonate, and ferric oxide, and mixtures thereof, and others. The addition of one or more of such ingredients may be beneficial to further facilitate ruminal bypass and/or to facilitate the release and/or the digestion and/or the degradation, in the abomasum and lower intestine, of the NPN compound and/or derivatives thereof. The skilled person knows how to select suitable ingredients to achieve this purpose.

Alternatively, when preparing the composition as taught herein, it may also be advantageous (although not essential) to add other ingredient(s) such as one or more ingredients selected from binding substances (e.g. cellulose derivatives such as hydroxypropylcellulose, methyl cellulose, sodium carboxymethylcellulose, vinyl derivatives such as polyvinyl alcohol or polyvinylpyrrolidone, gum arabic, guaiac gum, sodium polyacrylate, and the like), filling substances (e.g. starch, proteins, crystalline cellulose and the like), inert ingredients (e.g. silica and silicate compounds), flow-control substances that help the formation of pellets (wheat middlings, beet pulp, and the like), preservative agents (propionic acid or its salt, sorbic acid or its salt, benzoic acid or its salt, dehydroacetic acid or its salt, parahydroxybenzoic acid esters, imazalil, thiabendazole, orthophenyl phenol, sodium orthophenylphenol, diphenyl, and others compounds and mixtures thereof), antibacterial agent, and other compounds, may be added to prepare the ruminant feed or feed supplement compositions as taught herein. The skilled person is familiar with techniques and compounds which are useful to achieve these purposes, and which are compatible with the production of the ruminant feed or feed supplement compositions taught herein.

It may also be advantageous (but not essential) to further enhance the nutritional value and/or the therapeutic value the compositions as taught herein by adding further feed ingredients (e.g. nutritional ingredients, veterinary or medicinal agents etc.) or other ingredients to the compositions as taught herein.

For instance, one or more ingredients selected from grain products, plant products, animal products, proteins (e.g. protein ingredients as obtained from sources such as dried blood or meat meal, meat and bone meal, cottonseed meal, soybean meal, rapeseed meal, sunflower seed meal, canola meal, safflower meal, dehydrated alfalfa, corn gluten meal, soybean protein concentrate, potato protein, dried and sterilized animal and poultry manure, fish meal, fish and poultry protein isolates, crab protein concentrate, hydrolyzed protein feather meal, poultry byproduct meal, liquid or powdered egg, milk whey, egg albumen, casein, fish solubles, cell cream, brewer's residues, and the like), mineral salts, vitamins (e.g. thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g. water-soluble and water-insoluble monosaccharides, disaccharides, and polysaccharides), veterinary compounds (e.g. promazine hydrochloride, chloromedoniate acetate, chlorotetracycline, sulfamethazine, monensin, sodium monensin, poloxaline, oxytetracycline, BOVATEC, and the like), antioxidants (e.g. butylated hydroxyanisole, butylated hydroxytoluene, tertiary-butylhydroquinone, tocopherols, propyl gallate and ethoxyquin), trace element ingredients (e.g. compounds of cobalt, copper, manganese, iron, zinc, tin, nickel, chromium, molybdenum, iodine, chlorine, silicon, vanadium, selenium, calcium, magnesium, sodium and potassium and the like), and other compounds or ingredients, may be added to the feed or feed supplement compositions as taught herein.

The skilled person is familiar with methods and ingredients that are suitable to enhance the nutritional and/or therapeutic or medicinal value of ruminant feeds and feed supplements, and knows how to enhance the nutritional and/or therapeutic or medicinal value of the compositions as taught herein.

METHODS OF THE INVENTION

In further aspects, the present invention relates to a method improving nitrogen utilization from a NPN compound by a ruminant, in particular for increasing digestibility of fibres in a ruminant and/or for increasing somatic growth in a ruminant and/or for increasing food intake in a ruminant and/or for increasing milk production in a lactating ruminant and/or for reducing nitrogen (N) excretion in a ruminant and/or for improving rumen pH stability in a ruminant and/or for reducing ammonia toxicity in a ruminant, comprising the step of:
Administering to said ruminant a ruminal bypass NPN composition comprising a NPN compound and a rumen bypass agent, said rumen bypass agent allowing at least 50%, such as at least 60%, at least 65%, at least 70%, at least 75%, at least 80%, at least 85%, at least 90%, or more, bypass of the rumen.

In a further aspect, the present invention relates to a method for feeding a ruminant, said method comprising the step of replacing a portion of vegetables proteins by a composition comprising a NPN compound and a rumen bypass agent, said rumen bypass agent allowing at least 50% bypass of the rumen.

In an embodiment, between 10% and 100% of vegetable proteins may be replaced by the NPN composition as taught herein, per day. For instance, it may be advantageous to replace protein sources, such as soybean meal and the like, by administering a ruminant with the NPN composition comprising a NPN compound and a rumen bypass agent, said rumen bypass agent allowing at least 50% bypass of the rumen since protein sources (e.g. soybean meal and others) are generally expensive. For example, for grazing ruminants where the NPN composition taught herein may be the only supplemental nitrogen source. This may be, for example, the case for ruminants held in harsh environmental conditions as taught herein, where the nutritional quality of the grass may be low.

Whereas previously it was recommended that NPN compound be administered to a ruminant in an amount below or not exceeding 1% of the total dry weight of feed per day, it was now found that the ruminal bypass NPN compositions taught herein may be administered in amounts greater than 1% of the total dry weight of feed per day, e.g., in amounts between 1% and 10%, between 1% and 8%, between 1% and 5%, or between 1% and 3%.

In a further aspect, the present invention relates to a method for preventing or reducing ammonia toxicity in a ruminant, said method comprising the step of
administering to said ruminant a composition comprising a NPN compound and a rumen bypass agent, said rumen bypass agent allowing at least 50% bypass of the rumen.

In an embodiment, the NPN compound may be selected from the group consisting of urea, biuret, ammonium acetate, ammonium sulfate, ammonium butyrate, methylene urea, ammonium salt of an amino acid, acetamide, ammonia, butryamide, creatine, creatinine, dicyanoamide, formamide, ethylene urea, isobutanol diurea, lactosyl urea, propionamide, uric acid and urea phosphate. Suitable ammonium salts also include, for example, acetate, bicarbonate, carbamate, carbonate, chloride, citrate, formate, furmerate, lactate, maleate, phosphate, polyphosphate, propionate, succinate and sulfate ammonium salts, or any other suitable salt. In a preferred embodiment, the NPN compound may be urea and/or ammonia sulphate, more preferably urea.

In one embodiment, the composition as taught herein may comprise one or more NPN compounds selected from the group consisting of urea, biuret, ammonium acetate, ammonium sulphate, ammonium butyrate, methylene urea, ammonium salt of an amino acid, acetamide, ammonia, butryamide, dicyanoamide, formamide, ethylene urea, isobutanol diurea, lactosyl urea, propionamide, uric acid and urea phosphate. Suitable ammonium salts also include, for example, acetate, bicarbonate, carbamate, carbonate, chloride, citrate, formate, furmerate, lactate, maleate, phosphate, polyphosphate, propionate, succinate and sulphate ammonium salts, or any other suitable salt. The composition as taught herein may comprise urea and ammonium sulphate.

In one embodiment, any ruminal bypass agent that allows at least 50% bypass of the rumen may be used in the NPN compositions. Ruminal bypass agents that allow least 50% bypass of the rumen as well as methods to produce and use them for the purpose of bypassing the rumen are well known and commercially available. The skilled person knows how to prepare an effective ruminal bypass agent that allows at least 50% bypass of the rumen and that is suitable for the delivery of a NPN compound urea or ammonia to the abomasum and lower intestine of ruminants.

Non-limiting representative examples of ruminal bypass agents, which allow at least 50% bypass of the rumen include compositions comprising fatty acids (e.g. saturated or unsaturated fatty acid, essentially saturated fatty acids, short-chain fatty acids, medium-chain fatty acids, long-chain fatty acids, very-long-chain fatty acids or mixture thereof), compositions comprising partly or fully hydrogenated (or hardened) animal oils (beef tallow, yellow grease, sheep tallow, hog fat and others or mixture thereof), and compositions comprising partly or fully hydrogenated (or hardened) vegetable oils (e.g. palm oil, soybean oil, rapeseed oil, cottonseed oil, castor oil, and others or mixture thereof), and compositions comprising a mixture of two or more ingredients selected from fatty acids, partly or fully hydrogenated (or hardened) animal oils, and partly or fully hydrogenated (or hardened) vegetable oils, and other compounds.

in one embodiment, the NPN compound may orm a core that is coated with the ruminal bypass agent described above. The NPN compositions described above may also be referred to as a ruminal bypass NPN composition. The compositions as described above may be administered to a ruminant per se, or may be administered in admixture with other ingredients such as minerals, vitamins, antibiotics, and the likes. For example, the composition as taught herein may be incorporated in a feed composition or a feed supplement composition.

In an embodiment relating to the methods as taught above, the composition comprising a NPN compound and a rumen bypass agent that allow at least 50%, such as at least 60%, at least 65%, at least 70%, at least 75%, at least 80%, at least 85%, at least 90%, or more bypass of the rumen, may be a rumen bypass composition such as the one described herein, i.e., a ruminal bypass composition suitable for ingestion by a ruminant, comprising a core comprising more than 90 wt. % of a non-protein nitrogen (NPN) compound; and
a coating surrounding said core, said coating comprising or consisting of hydrogenated vegetable oil, which composition has a rate of release of NPN in the rumen of less than 5 wt. % per hour. In an embodiment, the hydrogenated vegetable oil may be selected from the group of hydrogenated palm oil, soybean oil, cotton seed oil, rapeseed oil, canola oil, peanut oil, corn oil, olive oil, sunflower oil, safflower oil, coconut oil, linseed oil, tung oil, and castor oil.

In a preferred embodiment, the hydrogenated vegetable oil is hydrogenated palm oil as mentioned beforehand.

The compositions as taught herein may be administered, according to the methods as taught herein, to a ruminant per se, or may be administered in admixture with other ingredients such as minerals, vitamins, antibiotics, and the likes. For example, the composition as taught herein may be incorporated in a feed composition or a feed supplement composition.

In an embodiment, the composition as taught herein may be administered by any known conventional methods suitable to feed ruminants. For instance, the composition as taught herein may be administered to said ruminant by allowing the ruminant to ingest the composition.

In a preferred embodiment, the composition as taught herein is administered to a ruminant orally.

In an embodiment, the NPN compositions as taught herein may be administered to a ruminant in an amount of about 0.0001% to about 1% of the animal body weight. For instance, the NPN compositions as taught herein may be administered to a ruminant in an amount of about 0.001% to about 0.5%, about 0.01% to about 0.1% of the animal body weight, preferably about 0.02% to about 0.09% of the animal body weight, preferably about 0.03% to about 0.08% of the animal body weight, preferably about 0.04% to about 0.07% of the animal body weight, preferably about 0.045% to about 0.06% of the animal body weight, more preferably about 0.048% to about 0.055% of the animal body weight.

In a preferred embodiment, the compositions as taught herein may be administered to a ruminant in an amount of about 0.05% of the animal body weight.

In an embodiment of the invention, the compositions as taught herein may be administered to a ruminant in an amount ranging between about 0.3 gram per day to about 3 kg per day, such as about 1 gram per day to about 1 kg per day, such as about 3 gram per day to about 800 grams per day, such as about 10 grams per day to about 500 grams per day, e.g., about 20 grams per day to about 400 grams per day, or about 30 grams per day to about 300 grams per day.

In a preferred embodiment, the NPN composition as taught herein may be administered in an amount ranging from about 30 grams per day to about 300 grams per day.

In another embodiment, the compositions as taught herein may be administered or fed to a ruminant ad libitum, i.e. at liberty, which means that the animal can eat as much as desired without any restrictions on the amount of the composition as taught herein that said animal may eat per day. It may be advantageous to administer the composition as taught herein ad libitum to a ruminant when the composition as taught herein is mixed with a complete feed or concentrate, for instance compound feed or total mixed ration.

In an embodiment, the composition as taught herein may be administered to a ruminant once every 3 days, preferably once every 2 days, more preferably once a day.

In an embodiment, the composition as taught herein may be administered once every week, once every 6 days, once every 5 days, once every 4 days, once every 3 days, once every 2 days, or once every day. In certain embodiment, it may be preferable to administer the composition as taught herein once a day.

In an embodiment, the composition as taught herein may be administered once every 3 days, once every 2 days, or once every day over an entire season, e.g. dry season. In certain embodiment, it may be preferable to administer the composition as taught herein once a day over an entire season, e.g. dry season.

In an embodiment, the composition as taught herein may be administered more than one times a day for instance 5 times per day, 4 times per day, 3 times per day or 2 times per day. It may be preferable to administer the composition as taught herein more than one time per day when the composition as taught herein is intended to replace the true protein ration.

The present inventors found that the compositions and methods as taught herein are advantageous for ruminants held under any climate, but particularly for ruminants held under harsh climates (e.g. hot and/or dry climates such as tropical climates). For instance, farms located in tropical countries are often remote (far in distance) from the areas where the ruminants (e.g. beef cattle) are kept. Such situation makes it difficult for farmers or caretakers to reach ruminants on a daily basis (i.e. ruminants may not be provided with supplemental feeds on a daily basis). The methods as taught herein provide a solution to this problem by allowing feeding events to be intermittent, e.g. feeding events may occur once every 2 or 3 days, while still increasing or promoting fiber digestibility and/or somatic growth and/or food intake in ruminants or cattle animals.

In an embodiment, the composition as taught herein may be administered to a ruminant according to the methods as taught herein, simultaneously with other conventional ruminant feeds and/or feed supplements (e.g. corn silage, alfalfa silage, mixed hay, grains, and the like) or may be administered separately, i.e. supplement offered in the pasture or compound feed offered during milking. In a preferred embodiment, the composition as taught herein may be administered to a ruminant separately from other conventional ruminant feeds and/or feed supplements.

In one embodiment, the composition as taught herein may be administered to a ruminant that is held outside for long periods of time, i.e., at least one week, two weeks, three weeks, 1 month, two months, three months, four months, or five or more months, in an environment suitable for grazing, such as pastureland or other fields with grass or other types of vegetation suitable for ruminants or cattle animals, during the rest of the day.

In one embodiment, the composition as taught herein may be administered to a ruminant held in an agricultural building (e.g. barn) or farm enclosure for long periods of time, i.e., at least one week, two weeks, three weeks, 1 month, two months, three months, four months, or five or more months.

In an embodiment, the ruminant is allowed to graze or feed ad libitum.

In one embodiment, the ruminant may be any ruminant selected from the group consisting of bovine, ovine, and caprine.

The bovine, ovine, and caprine may be a domestic or a wild animal and may be a male or a female (particularly a lactating female).

In a preferred embodiment, the bovine and/or ovine and/or caprine is a domestic animal.

In an embodiment, the bovine may be selected from the group consisting of cows, bulls, steers, stags, heifers, oxen, calves, and the like. In a preferred embodiment, the bovine is a bull, steer or heifer (beef). In another preferred embodiment, the ruminant is a bovine, preferably beef and/or a lactating cow.

In another preferred embodiment, the bovine is a cow, preferably a lactating cow.

In an embodiment, the ovine may be selected from the group consisting of sheep, mouflon, urial, and the like. In a preferred embodiment, the ovine is a sheep or a lamb. In another preferred embodiment, the ovine is a ewe, preferably a lactating ewe.

In an embodiment, the caprine may be selected from the group consisting of goats, ibex, markhor, and the like. In a preferred embodiment, the caprine is a goat. In another preferred embodiment, the caprine is a doe or nannie, preferably a lactating doe or lactating nannie.

In an embodiment, the ruminant may be of the genus *Bos*, such as *Bos Taurus* or *Bos indicus*, or the like. The ruminant may be cattle or cattle animal. In one embodiment, the cattle may be any cattle selected from the group consisting of cow cattle, beef (or bull) cattle, steer cattle, stag cattle, heifer cattle, oxen cattle, sheep cattle, goat cattle and the like. In a preferred embodiment, the cattle may be beef cattle. In another preferred embodiment, the cattle may be a cow cattle, preferably a lactating cow cattle.

In an embodiment, the compositions and methods as taught herein may be particularly suitable for improving nitrogen utilization from a NPN compound in a ruminant, for the purpose of, for instance, increasing digestibility of fibres in a ruminant and/or for increasing somatic growth in a ruminant and/or for increasing food intake in a ruminant and/or for increasing milk production in a lactating ruminant and/or for reducing nitrogen excretion in a ruminant and/or for improving rumen pH stability in a ruminant and/or for preventing and/or reducing ammonia toxicity in the rumen in ruminants in general or in ruminants held under any types of harsh climates, e.g., an Am climate (tropical monsoon climate) or an Aw climate (tropical wet and dry or savannah climate).

In an embodiment, the NPN compositions and methods as taught herein may be particularly suitable for improving nitrogen utilization from a NPN compound in a ruminant, for the purpose of, for instance, increasing digestibility of fibres in a ruminant and/or for increasing somatic growth in a ruminant and/or for increasing food intake in a ruminant and/or for increasing milk production in a lactating ruminant and/or for reducing nitrogen excretion in a ruminant and/or for improving rumen pH stability in a ruminant and/or for preventing and/or reducing ammonia toxicity in the rumen in ruminants held at a remote location. In the present invention, the term 'remote location' as used herein refers to a situation where ruminants are left grazing in a field or pastureland that is located far, e.g., at least 3, 4, 5, 6, 7, 8, 9, 10, or more Km away, from a farm or a care provider (e.g. farmer). When compared to ruminants held at a location more proximate to a farm, e.g. less than 3, 2, 1, or 0.5 Km away, or a care provider (e.g. farmer), ruminants held at a remote location may be disadvantaged because remote distances impede a farmer's ability or other caretaker's ability to reach said ruminants to provide feed and/or feed supplements. This may be particularly problematic when ruminants are held at a remote location in addition to being held under a harsh climate (e.g. Aw or Am climates).

In an embodiment, the methods and NPN compositions as taught are suitable for ruminants raised in environments wherein the temperature and/or humidity conditions vary over time, for instance in climates characterized by a dry season and a wet season (e.g. Aw climates).

In an embodiment, the methods as taught are suitable for ruminants raised in environments characterized by a pronounced dry season, which occurs in winter with the driest month having precipitation less than 60 mm and less than 1/25 of the total annual precipitation.

The present invention is further illustrated, but not limited, by the following examples. From the above discussion and these examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. All references referred to herein are incorporated by reference.

EXAMPLES

Example 1

Figure 1:
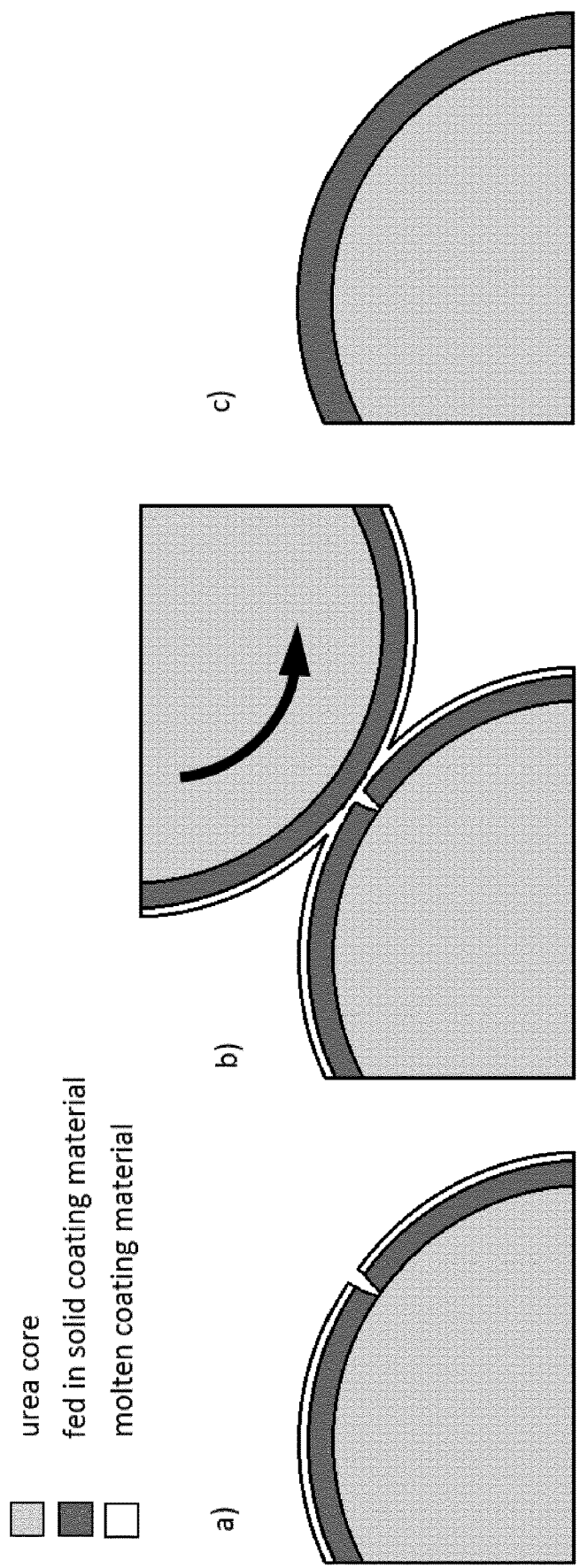
FIG. 1: illustrates the sealing of cracks by drum coating.
Figure 2:
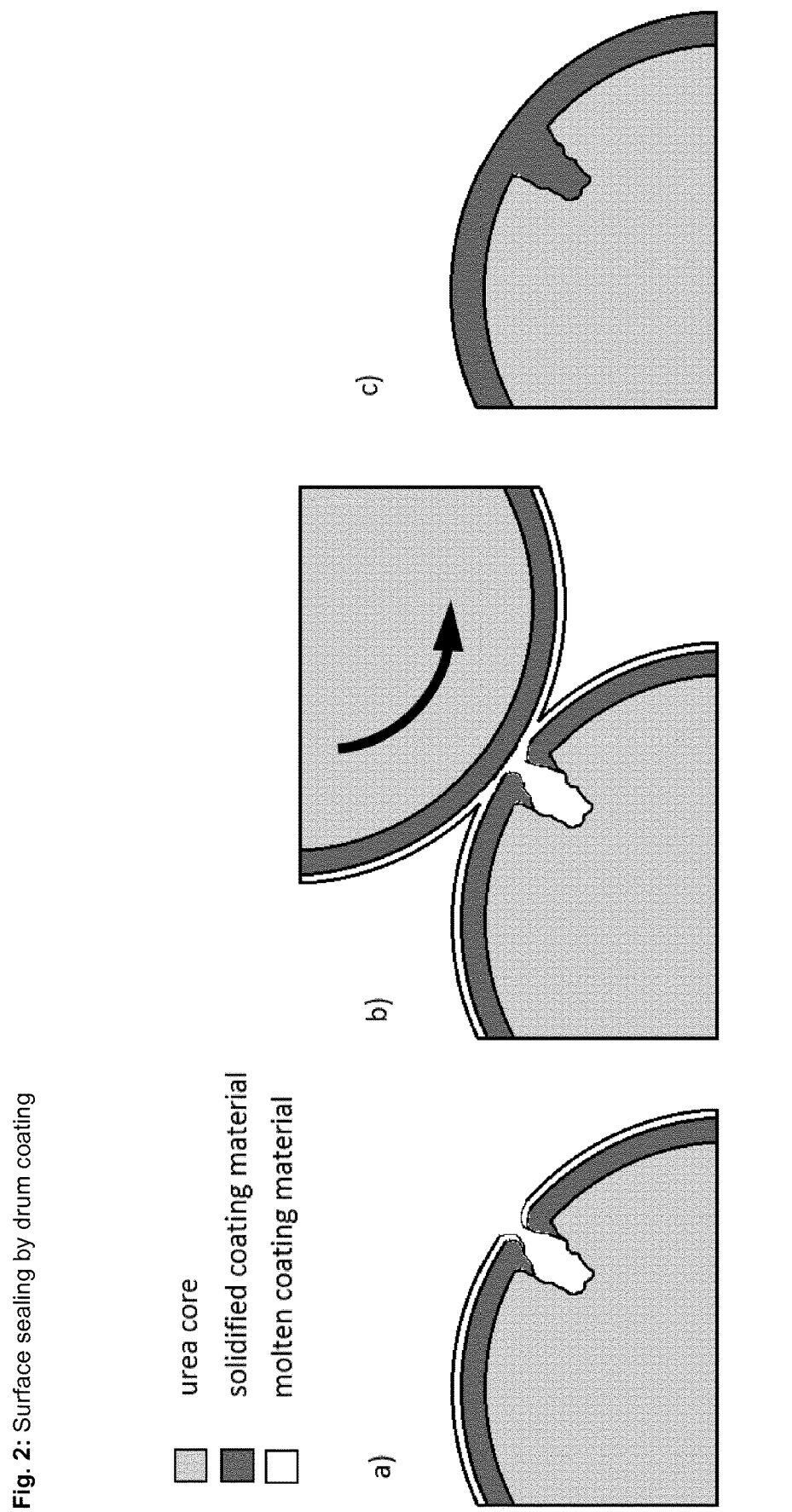
FIG. 2: illustrates the sealing of surfaces by drum coating.
Figure 3:
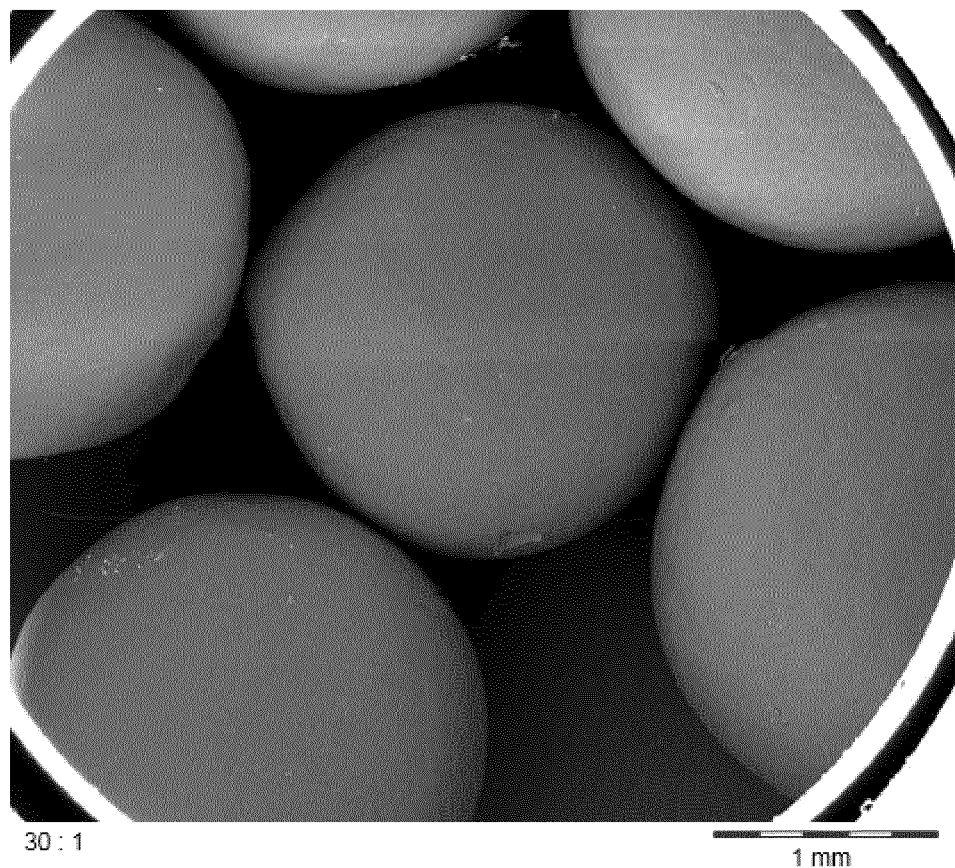
FIG. 3: SEM picture of the product of example 1 (30-fold magnification)
All SEM pictures were made using a Jeol scanning electron miscroscope, type JSM-7600F at an acceleration voltage of 20 kV.
Figure 4:
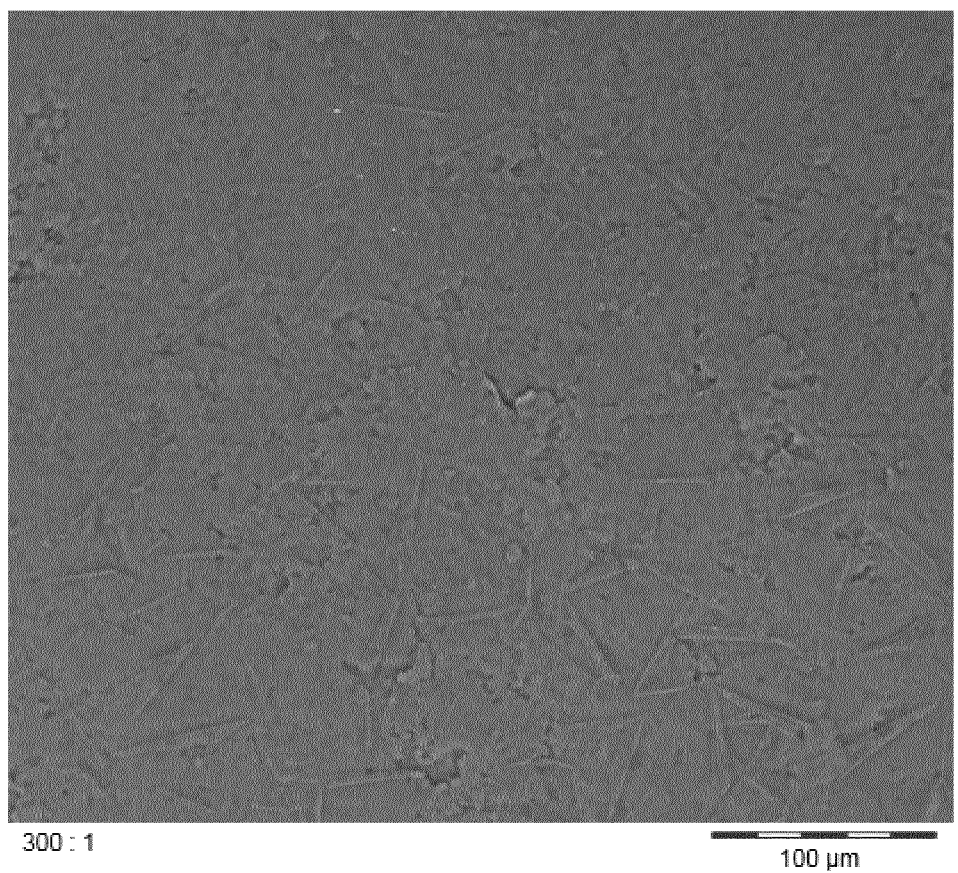
FIG. 4: SEM picture of the product of example 1 (300-fold magnification)
Figure 5:
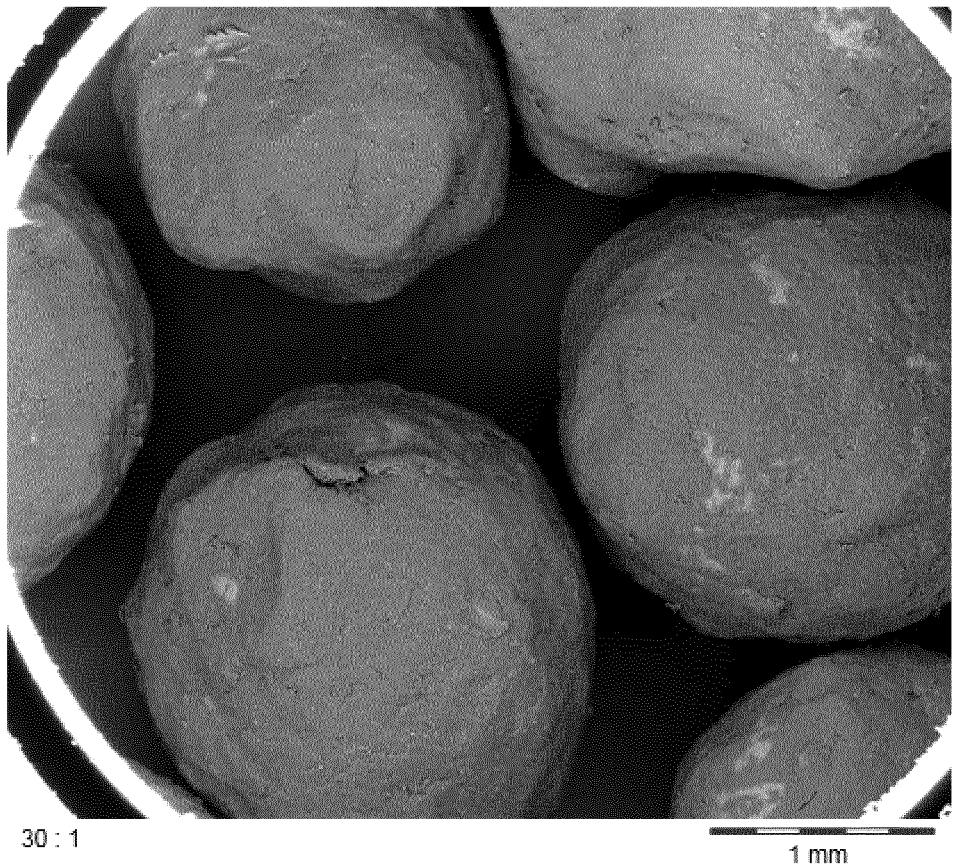
FIG. 5: SEM picture of the product of comparative example 2 (30-fold magnification)
Figure 6:
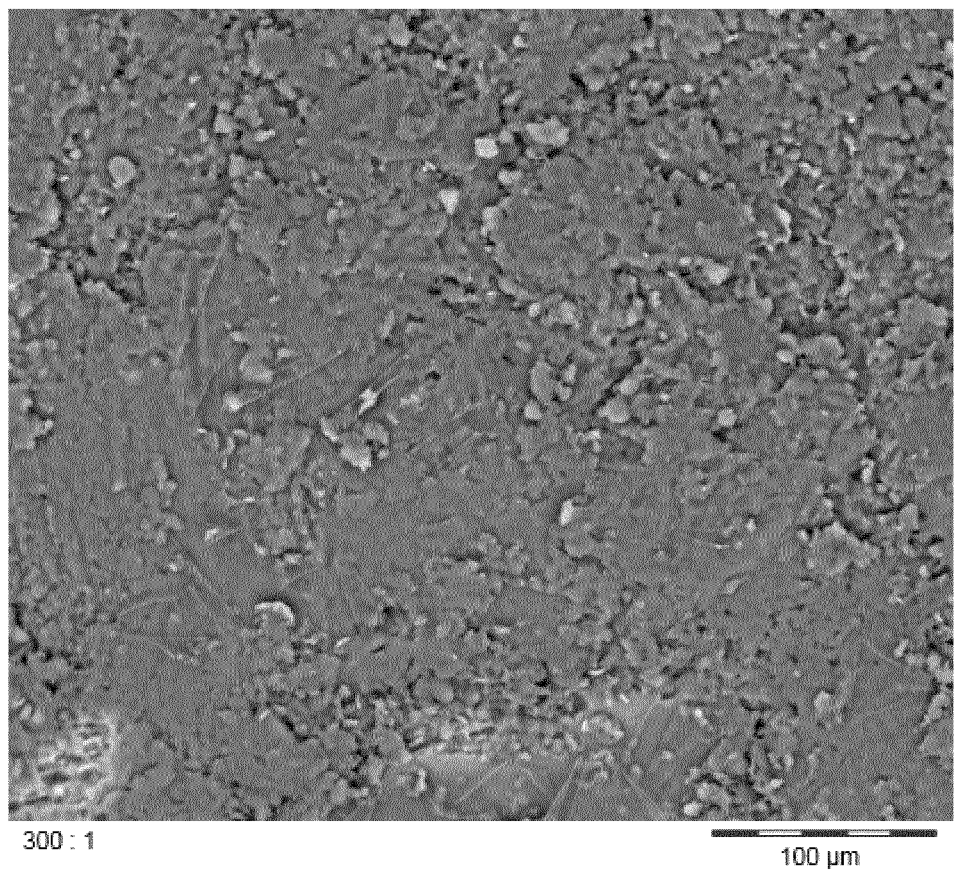
FIG. 6: SEM picture of the product of comparative example 2 (300-fold magnification)
Figure 7:
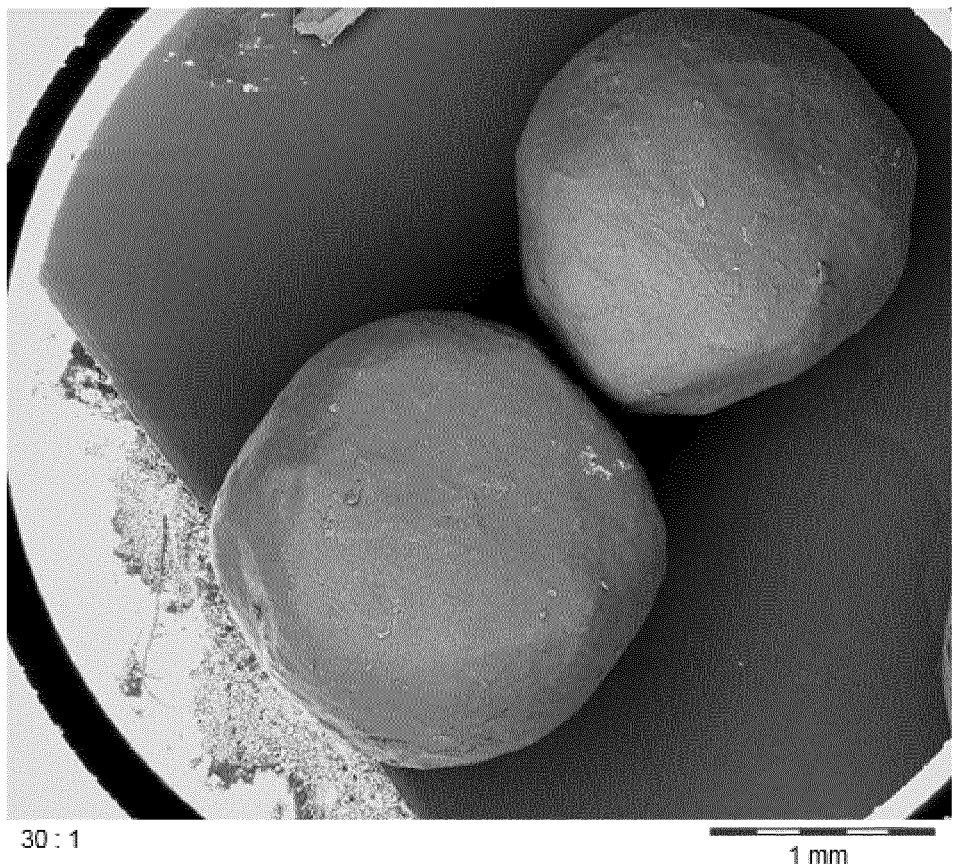
FIG. 7: SEM picture of the product of comparative example 3 (30-fold magnification)
Figure 8:
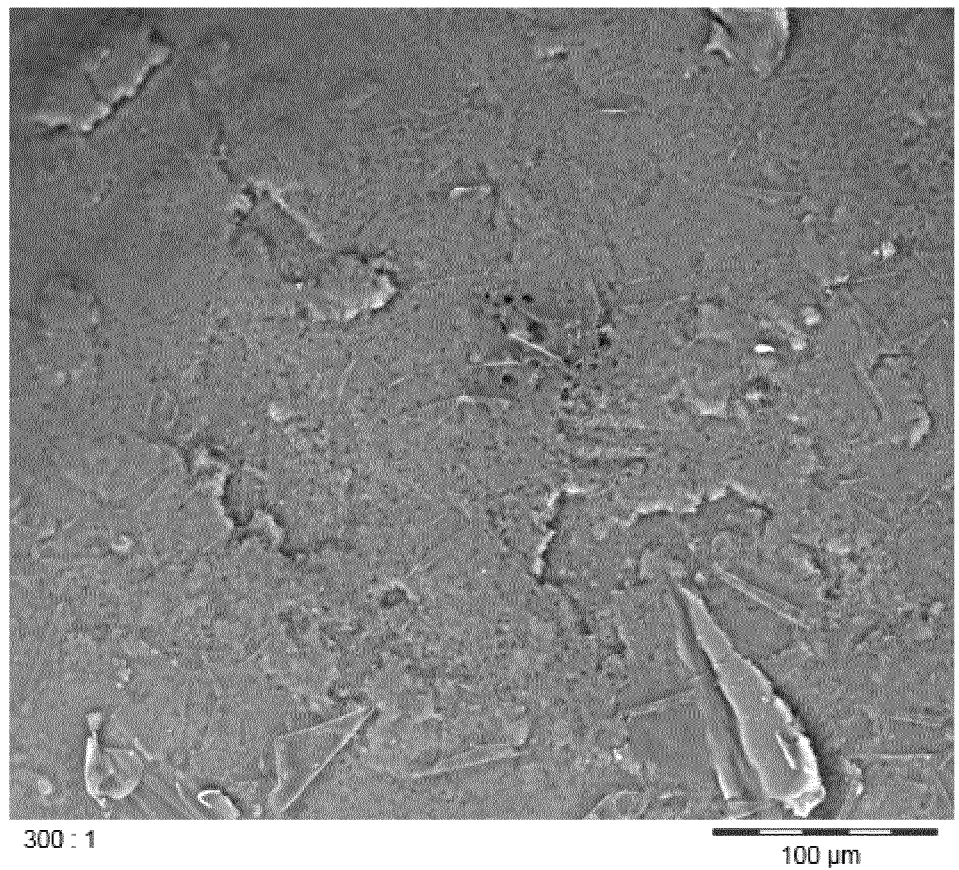
FIG. 8: SEM picture of the product of comparative example 3 (300-fold magnification)
Figure 9:
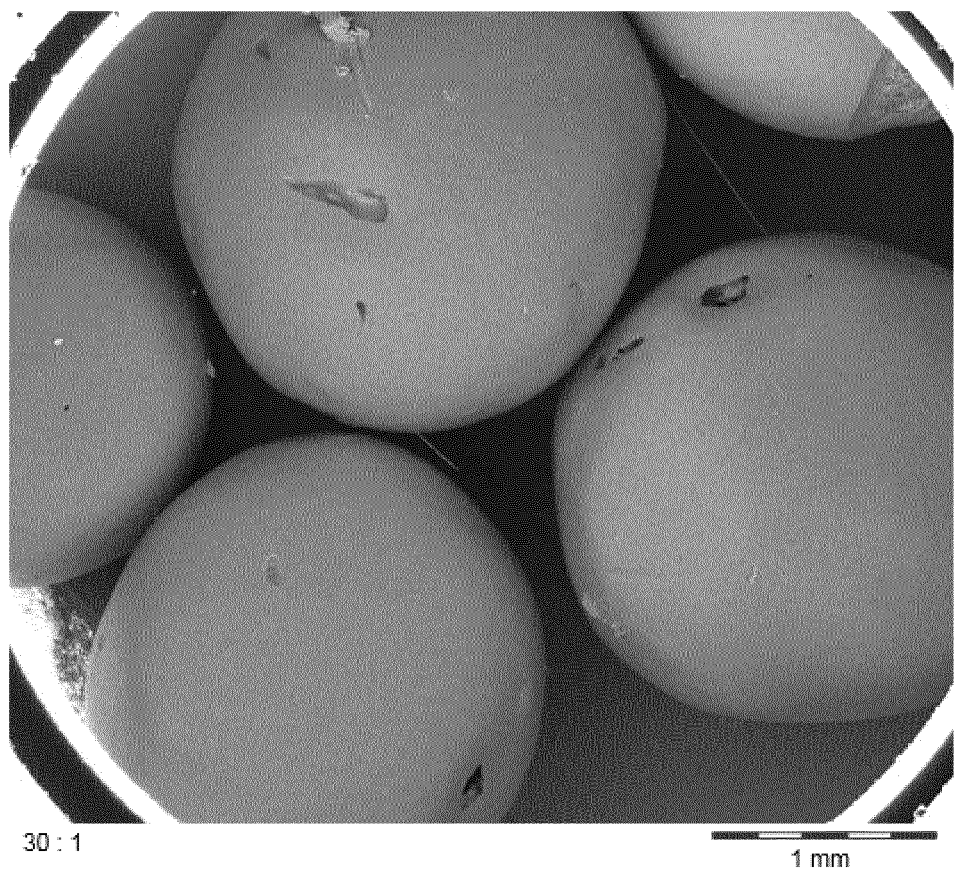
FIG. 9: SEM picture of the product of comparative example 4 (30-fold magnification)
Figure 10:
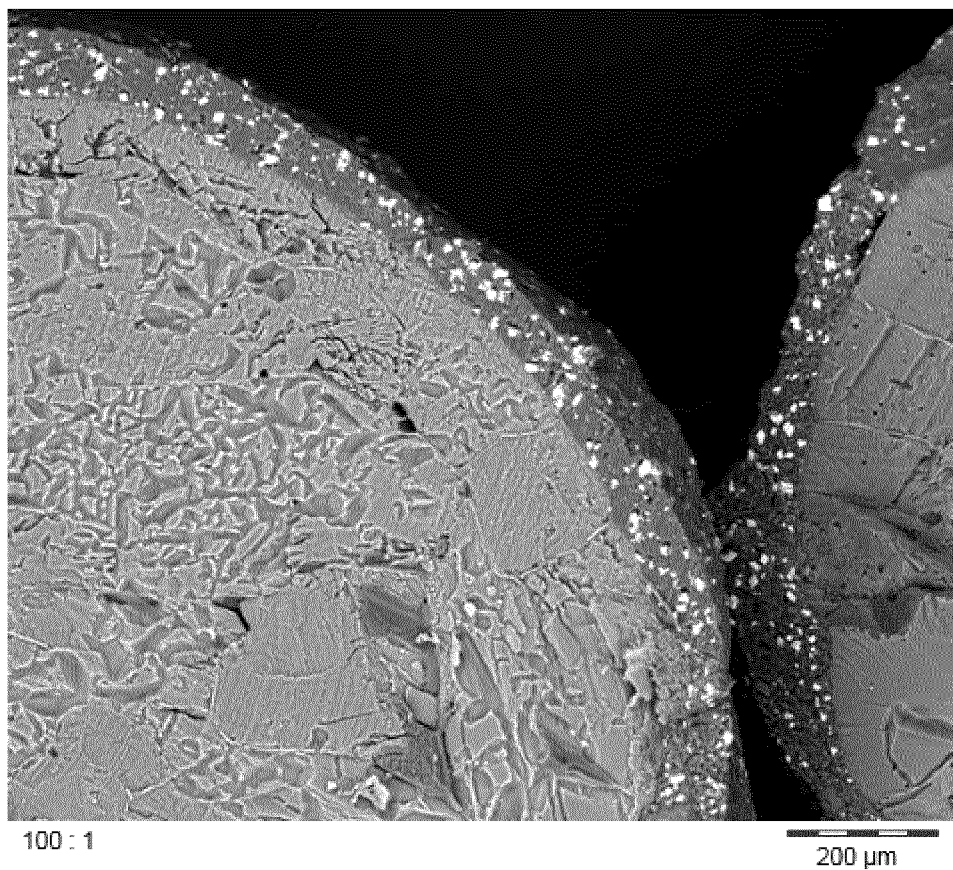
FIG. 10: SEM picture of the product of example 7 (100-fold magnification)
Figure 11:
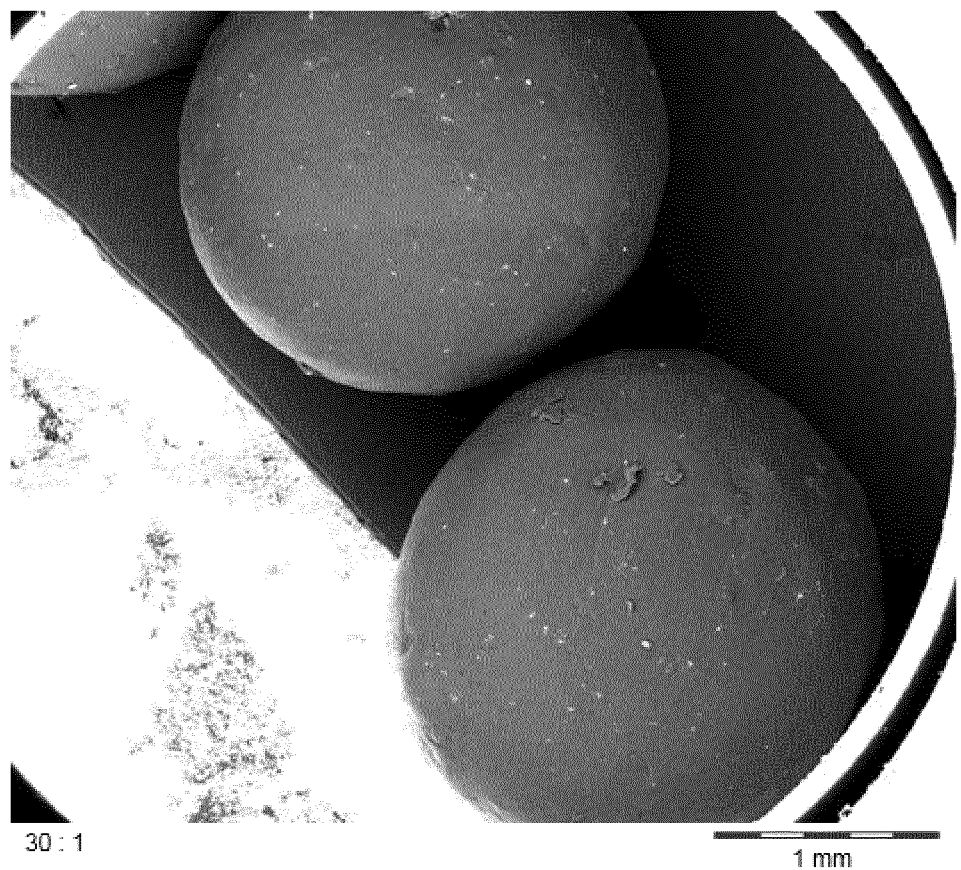
FIG. 11: SEM picture of the product of example 9 (30-fold magnification)
Figure 12:
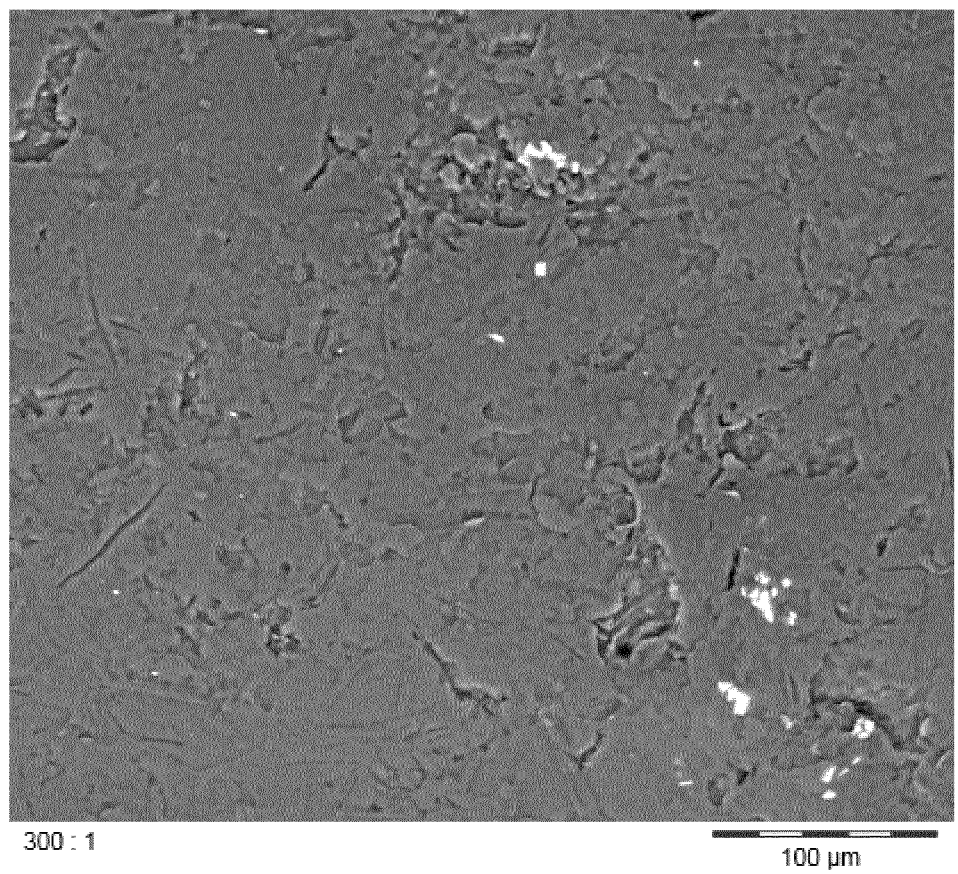
FIG. 12: SEM picture of the product of example 9 (300-fold magnification)
Figure 13:
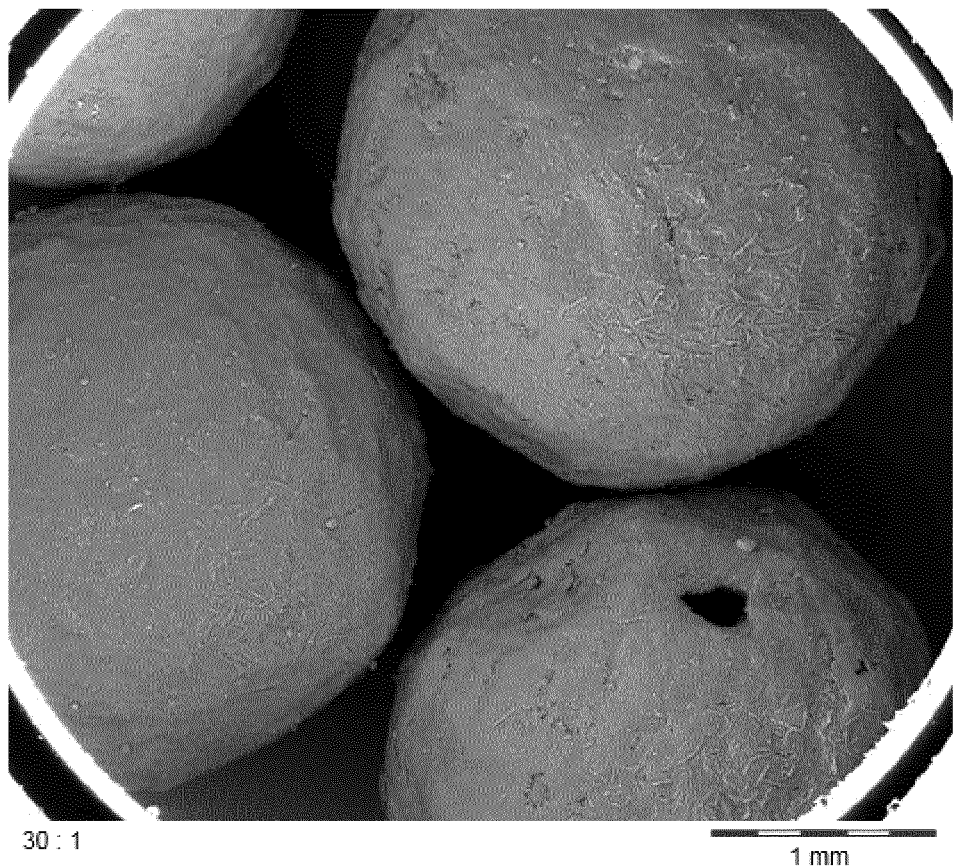
FIG. 13: SEM picture of the product of comparative example 11 (30-fold magnification)
Figure 14:
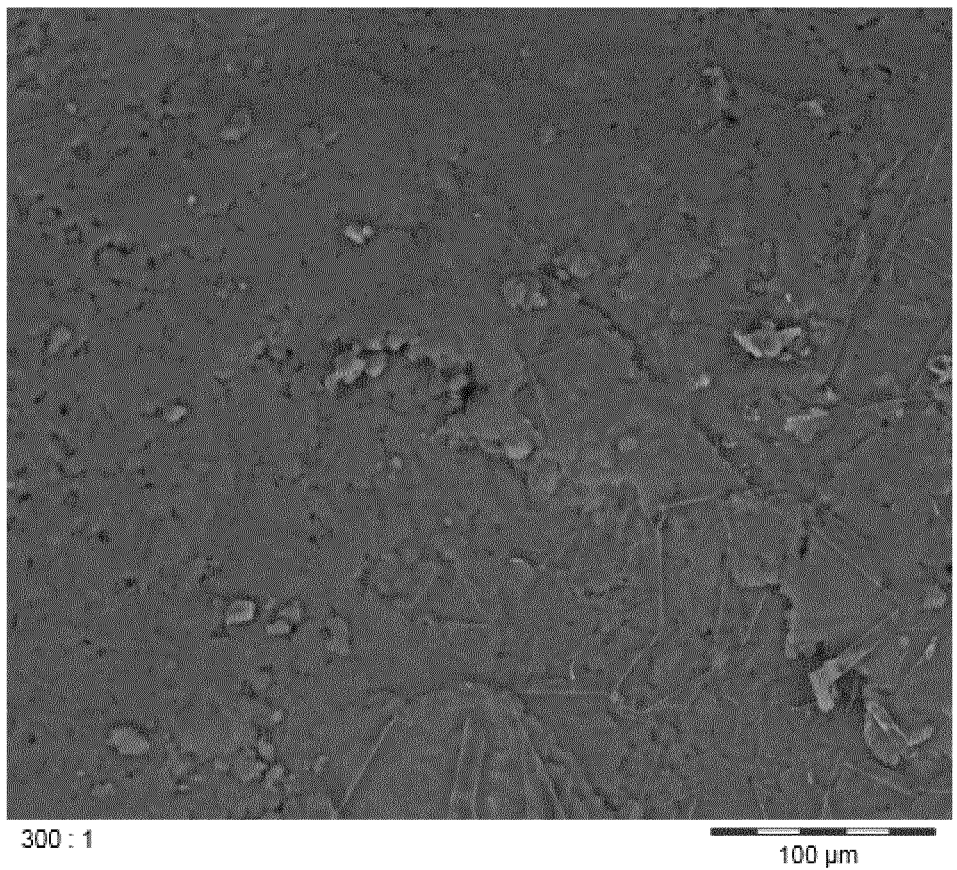
FIG. 14: SEM picture of the product of comparative example 11 (300-fold magnification)
Figure 15:
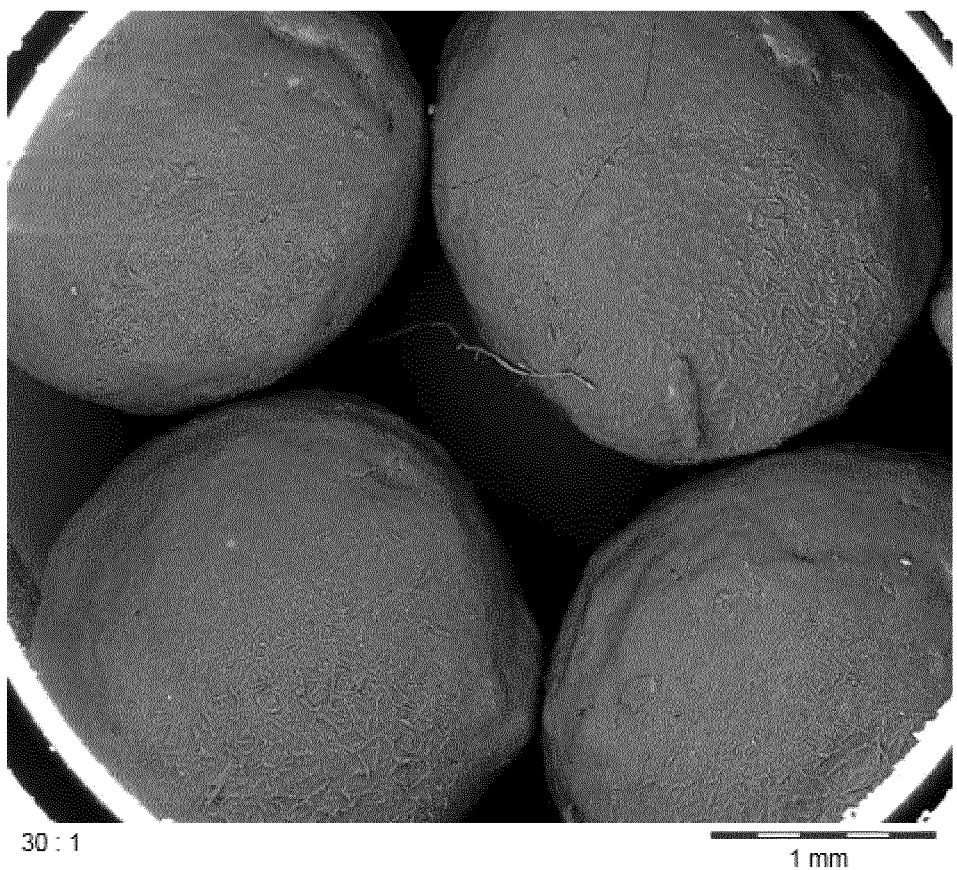
FIG. 15: SEM picture of the product of comparative example 12 (30-fold magnification)
Figure 16:
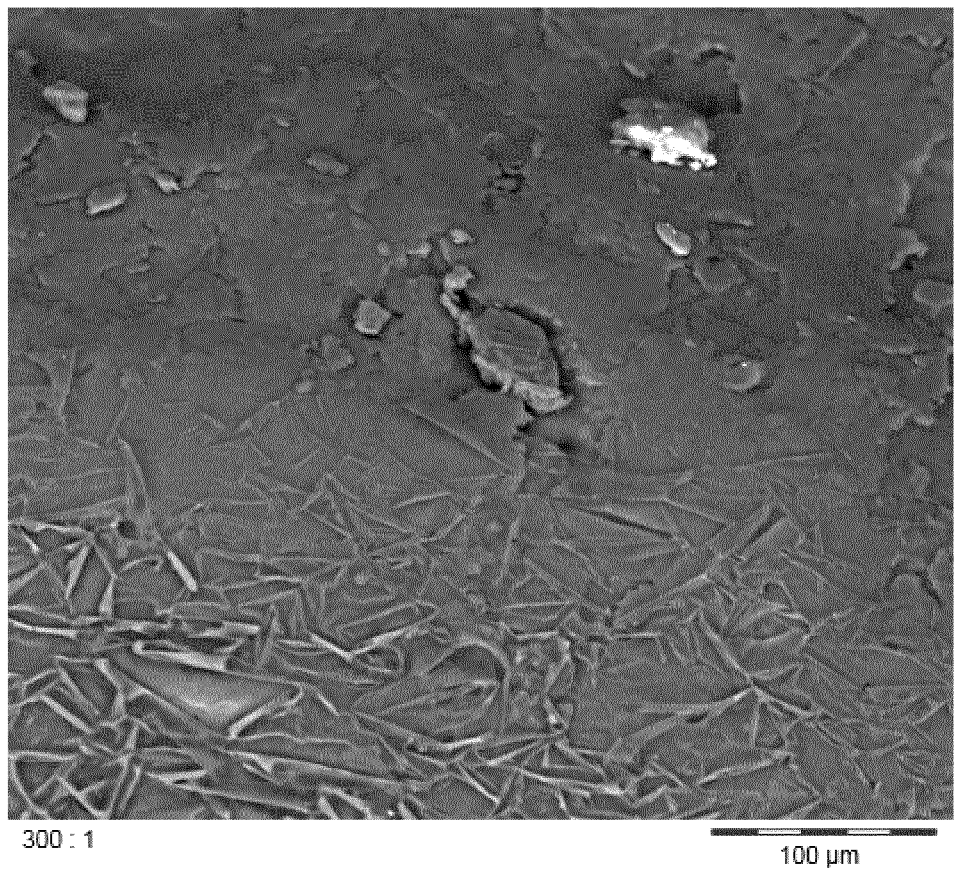
FIG. 16: SEM picture of the product of comparative example 12 (300-fold magnification)

Effects of Post-Ruminal Supply of a Urea Composition on Fiber Digestibility

Materials and Methods

The objective of this experiment was to evaluate the effects of ruminal versus abomasal infusion of urea on fiber digestibility in ruminants. The experiment included a four-week adaptation period to a basal diet (in this case mimicking a winter tropical diet (winter tropical climate being an Aw climate) in addition to the distinct experimental periods (i.e. one experimental period per treatment regimen listed in Table 1), each lasting fourteen days.

Animal Description and Number

Four non-lactating, non-pregnant Holstein heifers were used for the experiment. The Holstein heifers were on average 20±0.5 months of age and weighed on average 561±42 kg. Each heifer was rumen-cannulated. A tube was inserted into the abomasum via the rumen cannula to bypass the rumen.

Treatments

The experiment consisted of two treatment groups subjected to different treatment regimens. Specifically, each treatment group differed with respect to the delivery site (i.e. either in the rumen or abomasum) and administration regimen (i.e. either over 24 hours or once a day)(see Table 1 below).

Both treatment groups received an equal amount (127 g) of urea per day (as a source of non-protein nitrogen). Said amount of urea was calculated to enable the production of about 370 grams of crude protein (CP) per heifer, per day. Further, the amount of urea supplementation (i.e. 127 grams per day) provided 65% and 45% of rumen degradable protein (RDP) and CP calculated requirements, respectively, for a growing heifer at an average daily gain (ADG) of 0.2 kilogram.

TABLE 1

| Treatment groups | |
| --- | --- |
| Treatment Groups | Treatment Regimens |
| Treatment1: The 'Urea in the Rumen' (UR) group. | Holstein heifers (n = 4) received an urea solution, which was infused into the rumen, once a day via a cannula. |
| Treatment 2: The 'Urea in the Abomasum' (UA) group. | Holstein heifers (n = 4) received an urea solution, which was infused into the abomasum over 24 hours via a cannula. |

Adaptation to the Basal Diet

In order to simulate a tropical (winter) climate diet (i.e. an Aw climate diet), an adaptation period of 3 weeks was implemented prior to initiating treatment (as described in Table 1) with urea. Specifically, heifers were fed a diet that consisted of a low quality hay, which comprised 6.0% crude protein; 70% neutral detergent fiber (NDF) and 42% acid detergent fiber (ADF). The low quality of the hay resulted in low fiber digestibility of the hay. Heifers received this low quality hay in addition to 2.0 kg compound feed adaptation on a daily basis for an extra 9 days, which resulted in a prolonged adaptation period (to about 4 weeks). After the adaptation period, the heifers were exposed to the treatment regimens (i.e. consecutively, starting with treatment 1 and followed by treatment 2) as described in Table 1 (2 weeks per treatment regimen).

Animal Management

Heifers were housed in a tie-stall barn with individual water and feed troughs, rubber mattresses, and wood shaving bedding. The tie-stall was cleaned and the wood shaving replaced daily. Heifers were fed low quality hay twice a day (08 h 30 and 16 h 30). The heifers were allowed to eat ad libitum during both feeding events.

An amount of one kilogram of compound feed (referred to as the 'compound feed trial'), as a meal, was given in the morning (08 h 30) through the cannula (see Table 2). The details over the compositions of hay and compound feed ('compound feed adaptation' and 'compound feed trial') are presented in Table 3 below. Animals had free access to water troughs throughout the day.

TABLE 2

| Infusion site and composition | | |
| --- | --- | --- |
| Treatment | Sites of Infusion Rumen (infused once a day at 08h30) | Abomasum (infused over 24 h) |
| UR | 1 Kg CF + 127 g urea | NaCl 9 g/L |
| UA | 1 kg CF | Urea 12.8 g/L + NaCl 9 g/L |

Abbreviations:
UR = urea in rumen; UA = urea in abomasum; CF = compound feed.

TABLE 3

| Compound feed and hay composition | | | |
| --- | --- | --- | --- |
| Ingredients (g/Kg) | CF Adaptation | CF Trial | Hay |
| Corn | 240 | 625 | — |
| Soybean meal | 654 | 330 | — |
| Feed grade Ca carbonate | 1.6 | 1.5 | — |
| NaCl | 0.5 | 0.42 | — |

TABLE 3-continued

Compound feed and hay composition

| | | | |
|---|---|---|---|
| MgSO$_4$ | 0.5 | 0.48 | — |
| Mono CaPO$_4$ | 1.2 | 1.08 | — |
| MgO$_2$ | 0.6 | 0.54 | — |
| Urea | 6.2 | 0.00 | — |
| VM Vit. E/SE mix RuBB600[1] | 0.12 | 0.12 | — |
| FF VM 2619 Vit E (0.025%)[2] | 0.12 | 0.12 | — |
| FF 15073 Melkvee Std. Bulk[3] | 0.24 | 0.24 | — |

| Chemical composition | CF adaptation | CF Trial | Hay |
|---|---|---|---|
| DM (g/Kg) | 893 | 880 | 873 |
| OM (g/Kg DM) | 920 | 930 | 945 |
| CP (g/Kg DM) | 481 | 217 | 60.8 |
| EE (g/Kg DM) | 24.6 | 29.6 | 10.7 |
| NFD (g/Kg DM) | 115 | 114 | 700 |
| ADF (g/Kg DM) | 70.3 | 47.2 | 421 |
| Lignin (g/Kg DM) | n.a | n.a. | 518 |

Abbreviations:
[1] Ca, 159 g; P, 6.47 g; Na, 0.27 g; Mg, 2.71 g; K, 7.14 g; S, 0.9 g Cl, 0.70 g; Cu, 0.65 mg; Zn, 7.99 mg; Fe, 12.5 mg; Se, 87.0 mg; Vitamin E, 43478 I.E./
[2] Ca, 331.369 g; Mg, 2,516 g; Vitamin E, 100000 I.E./
[3] Ca, 376 g; Na, 0.07 g; Mg, 3.00 g; S, 2,54 g; Cu, 5.00g; Mn, 5.00 g; Zn, 10.0 g; Se, 133 mg; Co, 95.0 mg; Vitamin A, 2500000 I.E.; Vitamin D, 500000 I.E.
DM = dry matter, OM = organic matter, CP = crude protein, EE = ether extract, NDF = neutral detergent fiber, ADF = acid detergent fiber, and n.a. = non-available.
'CF Adaptation' refers to CF used during the diet adaptation period while 'CF trial' refers to the CF used during the two experimental regimens listed in Table 1.
The symbol '-' under the column 'Hay' indicated that the rows are left intentionally blank because dried grass is the only constituent of hay.

Double Infusions

All heifers were simultaneously infused in the rumen and the abomasum. This experimental design allowed each heifer to receive every treatment (consecutively), which provided 4 replicates per treatment. The two experimental periods described in Table 1 lasted 14 days each. For each individual treatment regimen, the fourteen-day period consisted of 8 days of adaptation, 4 days for sampling, and 2 days of rest without any infusions.

Whenever the treatment solution was infused in the rumen, a placebo solution (e.g. saline solution) was infused in the abomasum and whenever the treatment solution was infused in the abomasum, a placebo solution (e.g. water) was infused in the rumen. In the present case, it was necessary to infuse a saline solution in the abomasum (as opposed to water) in order to avoid problems related to osmotic pressure due to the small volume of the abomasum. This situation requires the use of a solution, which has an osmotic pressure similar to that of blood. A physiological saline solution fulfils this requirement. Contrary to the situation in the abomasum, infusion of a saline solution is not required for the rumen because the latter has a much larger volume, which does not create osmotic pressure problems. Therefore, infusion of water is suitable for the rumen.

Each heifer was equipped with two infusion lines via the cannula bung. Specifically, the first line delivered the solution straight into the rumen; the second line passed through the rumen into the omasum, using a rubber flange as anchor, delivering the pumped solution into the abomasum (Gressley et al. (2006)).

All eight infusion lines (2 per heifer) were connected to a single peristaltic pump (Watson-Marlow 520S) equipped with a pump-head of 10 cassettes (Watson-Marlow 505CA8). Infusion solutions were kept in 20 L capacity bottles, which were replaced every two days, after morning feeding.

Infusate levels and infusion rates were checked 3 times per day (at 09:00 h; 16:00 h and 21:00 h). Whenever necessary, manifold tubes with different inner diameter were replaced to adjust rate or level of solution, aiming to reach 10 L (or 5 L during the first two days of the period) infused continually in 24 h. The infusion rate was set at 3.5 mL/min (5 L/d) for the first two days of adaptation in each experimental period and 6.9 mL/min (10 L/d) for the remaining days.

Collection of Samples

Compound Feed and Hay

Samples of compound feed and hay were taken from day 09 to 12 of each experimental period. After samples were collected, a portion was used to determine dried matter content (DM) at 60° C. 72 h and the rest was stored at −20° C. in a large bag labelled with the period number and trial code. At the end of the period, dry samples were pooled and mixed thoroughly so as to obtain a composite sample for each period and was properly labelled with trial code and period. The samples were subsequently used to determine fiber digestibility.

Refusals

Leftovers of hay were determined and sampled from day 10 to 13 (the sampling days) of each experimental period. After samples were collected, a portion was used to determine DM at 60° C. 72 h and the rest were stored at −20° C. in a large bag labelled with the animal name, period and trial code. At the end of the period, dry samples were pooled and mixed thoroughly so as to obtain a composite sample for each period, and was properly labelled with trial code and period. The samples were subsequently used to determine food intake.

Faeces

Faecal samples were taken from the rectum according to the following schedule. On day 10 at 08:00 h and 14:00 h; day 11 at 10:00 h and 16:00 h: and day 12 at 12:00 h and 18:00 h. Samples were frozen, air-dried (60° C.; 72 h), and composite (pooled samples) faeces samples were prepared based on dry weight, for each animal, in each experimental period. Composite samples were labelled with trial code, period, and animal. The samples were subsequently used to determine fiber digestibility.

Fiber Digestibility Assessment

Fiber digestibility was determined based on the apparent indigestibility of feed using the method described in Casali et al., R. Bras. Zootec., Vol 37: 335-342 (2008).

Results

The results are presented in Table 4 below. The results show that the apparent fiber digestibility was increased in heifers which received urea supplementation in the abomasum compared to heifers which received urea supplementation in the rumen.

TABLE 4

Dry matter, organic matter, and neutral detergent fiber apparent fiber digestibility of Holstein heifers subjected to non-protein nitrogen infusions.

| | Treatments | |
|---|---|---|
| Apparent fiber digestibility (%) | UR | UA |
| Dry matter | 49.35 | 51.36 |
| Organic matter | 50.18 | 52.79 |
| Neutral detergent fiber | 43.75 | 48.27 |

Abbreviations:
UR = urea into rumen;
UA = urea into abomasum.

Example 2

Effects of Post-Ruminal Supply of a NPN Compound Composition on Feed Intake

The objective of this experiment was to evaluate the effects of ruminal versus abomasal infusion of ammonia (an equivalent source of NPN) on food intake in ruminants. The experimental procedure was the same as described above for example 1, except that ammonia was used instead of urea in an equivalent amount of N. The treatments consisted of continuous infusion of ammonia into the rumen or abomasum as depicted in Table 5.

TABLE 5

Infusion site and composition

| Treatment | Rumen (infused once a day at 08 h 30) | Rumen (infused over 24 h) | Abomasum (infused over 24 h) |
|---|---|---|---|
| AR | 1 kg CF | $NH_4OH$ 14.8 g/L | NaCl 9 g/L |
| AA | 1 kg CF | $H_2O$* | $NH_4OH$ 14.8 g/L + NaCl 9 g/L |

Abbreviations:
AR = ammonia in rumen;
AA = ammonia in abomasum;
CF = compound feed.
*Water in the same amount used to dilute ammonia solution in AR: 20 L/day

Feed Intake Assessment

In the present invention, feed intake was determined by weighting and recording, on a daily basis, the amount of feed (in this case hay) provided (typically provided at the beginning of the day around 8:30 AM) and the amount of leftover feed (i.e. feed not eaten, typically assessed at the beginning of next day around 8:00 AM) remaining in the trough (or feed holder). Feed intake was calculated according to the following formula:

Feed intake=[amount of feed provided at the beginning of the day]−[amount of feed left intact (i.e. not eaten) after a period of 24 hours]).

Results

The results are presented in Table 6 below. The results indicate an increase in feed intake of hay (see 'hay dry matter' in Table 6) as well as total nutrient (see 'total dry matter', 'organic matter', 'neutral detergent fiber', 'crude protein (feed)', and 'crude protein (total)' in Table 6) in heifers that were infused with ammonia as supplementary non-protein nitrogen source into abomasum relative to heifers that were infused with ammonia in the rumen.

TABLE 6

Hay and total nutrient intake of Holstein heifers subjected to administered with ammonia.

| | Treatments | |
|---|---|---|
| Feed intake (Kg/day) | AR | AA |
| Hay Dry Matter | 5.37 | 6.09 |
| Total Dry Matter | 6.26 | 6.97 |
| Organic Matter | 5.90 | 6.58 |
| Neutral detergent fiber | 3.87 | 4.38 |
| Crude Protein (Feed) | 0.537 | 0.581 |
| Crude Protein (Total) | 0.907 | 0.952 |

Abbreviations:
AR = ammonia in rumen;
AA = ammonia in abomasum

Example 3

Effects of Post-Ruminal Supply of a NPN Composition on Somatic Growth

The objective of this experiment is to evaluate the effects of ruminal versus abomasal infusion of urea on somatic growth in ruminants. The experimental procedure and animal treatments is the same as described above for example 1, except that the duration of the treatments is at least 2 months, such as 6 months.

Somatic Growth Assessment

Heifers are individually weighed on the first day of each experimental period (i.e. day 1) and on the last day of the experimental period (i.e., after at least 2 months, such as after 6 months). Changes in body weight are recorded for each heifer with respect to each treatment regimen (listed in Table 1) according to the following formula:

Somatic growth=[body weight before onset of treatment with urea or ammonia]−[body weight after termination of the treatment with urea or ammonia]).

An increase in body weight indicates an increase in somatic growth while a decrease or no change in body weight indicates a decrease in somatic growth or unchanged somatic growth, respectively.

Results

The results show that heifers which are infused with urea or ammonia in the abomasum display increased body weight at the end of the treatment with urea or ammonia compared to heifers which are receiving an equivalent amount of urea or ammonia in the rumen.

Example 4

Effects of Post-Ruminal Supply of a NPN Composition on Milk Production in Lactating Ruminants The objective of this experiment is to evaluate the effects of ruminal versus abomasal infusion of urea or ammonia on milk production in ruminants. The experimental procedure and animal treatments is the same as described above for example 1, except that the Holstein heifers were lactating heifers.

Results

The results show that lactating heifers which are infused with urea or ammonia in the abomasum display increased milk production at the end of the treatment with urea or ammonia compared to lactating heifers which are receiving an equivalent amount of urea or ammonia in the rumen.

Example 5

Preparation of a Rumen By-Pass Urea Formulation

A rumen by-pass urea formulation was prepared using a drum coater, equipped with a drop lance for addition of a molten oil or molten fat to a bed of urea particles. The drum coater had a diameter of ca. 350 mm and a drum width of ca. 190 mm. The width of the used bed was ca. 120 mm and the inflow area in which hot air was blown into the particle bed (inflow area) had a width of ca. 100 mm.

The drum coater was filled with 400 g of prilled urea having a particle size of from 1.8 to 2.4 mm. Then the interior of the drum coater was heated up with hot air until the bed of urea particles had a temperature of 48° C. In a double-walled vessel with a heater hydrogenated palm oil with a melting point of from 50 to 55° C. was molten and heated to a temperature of 65° C. The molten palm oil was pumped from the double-walled vessel through an electrically heated pipe into the drop lance. The molten palm oil was dropped from the drop lance onto the bed of prilled urea over a time period of 12 minutes at a radial speed of the stirrer of 32 meters per minute. During the addition of the molten palm oil the temperature of the bed of prilled urea was kept at a temperature of from about 48.0 to about 50.5° C. The temperate of the bed of prilled urea was determined by means of thermo-element which was held directly into the moved bed of particles. During the coating the bed of particles was tacky and the coating layers were formed slowly over time. After 12 minutes ca. 80 g of the molten hydrogenated palm oil was added and coated onto the urea particles, and the particle bed was allowed to cool down slowly. A dust-free product with a coating of 16.7 wt.-%, based on the total weight of the coated product, was obtained. The coated particles had a very smooth and shiny surface. Further, the obtained product consisted of particles of comparable size, it was free of any agglomerates or larger particles.

Comparative Example 6

Drum Mixer Coating

A horizontal mixer from Loedige with a volume of 10 liter, which was equipped with a Pflugschar® agitator, a double-jacket and a drop lance for the introduction of molten fat, was filled with 2 kg of prilled urea. Then the interior of the mixer was heated by the double jacket with hot water until the bed of pilled urea had a temperature of 45° C. and the prilled urea was moved with a radial stirrer speed of 30 meters per minute. Molten hydrogenated palm oil with a melting point of from 50 to 55° C. was heated to 65° C. and pumped from a double-walled vessel through an electrically heated pipe. By means of the drop lance 410 g of the molten fat was dropped onto the urea bed over a time period of 15 minutes at a radial speed of 30 meters per minute. During the coating process the particle bed was tacky. After addition of the hydrogenated palm oil the particle bed was allowed to cool down slowly. A dust-free product with a coating of 17 weight-%, based on the total weight of the coated product, was obtained.

Comparative Example 7

Fluidized Bed Coating 200 g of prilled urea with a particle size of 1.8 to 2.4 mm were placed in a Strea-1™ fluidized bed coater (Aeromatic-Fielder). The urea prills were fluidized by air having a temperature of 40° C. The coater was equipped with a nozzle on top for spraying molten hydrogenated palm oil onto the urea particles. Molten hydrogenated palm oil with a melting point of from 50 to 55° C. was heated to 70° C. and pumped from a double-walled vessel through an electrically heated pipe. The molten palm oil was sprayed onto the bed of the urea prills over a time period of 10 minutes. After addition of 13 wt.-% of hydrogenated palm oil, the product was cooled down by lowering the air temperature.

Comparative Example 8

Drum Coating at Lower Temperature

The same experimental setup as in example 5 was used. The drum coater was filled with 600 g of prilled urea having a particle size of from 1.8 to 2.4 mm. Then the interior of the drum coater was heated up with hot air. The bed of urea particles had a temperature of less than 40° C. In a double-walled vessel with a heater hydrogenated palm oil with a melting point of from 50 to 55° C. was molten and heated to a temperature of 65° C. The molten palm oil was pumped from the double-walled vessel through an electrically heated pipe into the drop lance. The molten palm oil was dropped from the drop lance onto the bed of prilled urea over a time period of 15 minutes at a radial speed of the stirrer of 32 meters per minute. During the addition of the molten palm oil the temperature of the bed of prilled urea was kept at a temperature of from about 40 to about 45° C. After addition of the hydrogenated palm oil the particle bed was allowed to cool down slowly. A dust-free product with a coating of 17 weight-%, based on the total weight of the coated product, was obtained. In contrast to the products of Example 1, the products of comparative Example 4 had a large fraction of agglomerates of two, three or even more particles.

Comparative Example 9

Drum Coating at Higher Temperature

The same experimental setup as in example 5 was used. The drum coater was filled with 600 g of prilled urea having a particle size of from 1.8 to 2.4 mm. Then the interior of the drum coater was heated up with hot air. The bed of urea particles had a temperature of 52° C. In a double-walled vessel with a heater hydrogenated palm oil with a melting point of from 50 to 55° C. was molten and heated to a temperature of 65° C. The molten palm oil was pumped from the double-walled vessel through an electrically heated pipe into the drop lance. The molten palm oil was dropped from the drop lance onto the bed of prilled urea over a time period of 15 minutes at a radial speed of the stirrer of 32 meters per minute. The bed temperature of the prilled urea was between 52 and 55° C. The experiment had to be stopped because the material inside the coater agglomerated completely and therefore, any mixing of the particle bed was no more possible.

Example 10

Preparation of a Rumen By-Pass Urea Formulation

The preparation of a rumen by-pass urea formulation was carried out in the same way as described in Example 5. 171 g of molten hydrogenated palm oil was coated onto 400 g of prilled urea having a particle size of 1.8 to 2.4 mm over a time period of 40 minutes. The temperature of the bed of urea particles was between 49.5 and 50.5° C. The dust-free product contained 70 wt.-% urea, the particles are very smooth and have a shiny surface. The product was free of any agglomerates or larger particles.

Example 11

Preparation of a Rumen By-Pass Urea Formulation

The preparation of a rumen by-pass urea formulation was carried out in the same way as described in Example 5 with the exception that a mixture of hydrogenated palm oil and calcium carbonate was used as coating material. A mixture of 80 g of molten hydrogenated palm oil and 48 g of a commercially available micronized calcium carbonate (type NOFACAL 0/50 from NOFAKALK GmbH, 95632 Wunsiedel-Holenbrunn, Rampenstrasse 4, Germany) with a particle size of from less than 5 µm to 60 µm was coated onto 400 g of prilled urea having a particle size of from 1.8 to 2.4 mm over 18 minutes. The bed temperature of the prilled urea was between 51 and 52° C. The dust-free product contained 75.8 wt.-% urea, particles were very smooth and had a faint surface. The product was free of any agglomerates or larger particles.

Example 12

Preparation of a Rumen By-Pass Urea Formulation

The preparation of a rumen by-pass urea formulation was carried out in the same way as described in Example 5. 120 g of molten hydrogenated palm oil was coated onto 400 g of prilled urea with a particle size of 1.8 to 2.4 mm over a time period of 25 minutes. The bed temperature of the prilled urea was between 50 and 52° C. The dust-free product contained 76.9% urea, the particles were very smooth and had a shiny surface. The product was free of agglomerates or larger particles.

Example 13

Preparation of a Rumen By-Pass Urea Formulation

The preparation of a rumen by-pass urea formulation was carried out in the same way as described in Example 5 with the exception that a mixture of hydrogenated palm oil and calcium carbonate was used as coating material. A mixture of 80 g of molten hydrogenated palm oil and 28 g of a commercially available micronized calcium carbonate (type NOFACAL 0/50 from NOFAKALK GmbH, 95632 Wunsiedel-Holenbrunn, Rampenstrasse 4, Germany) with a particle size of from less than 5 µm to 60 µm was coated onto 400 g of prilled urea having a particle size of from 1.8 to 2.4 mm over 30 minutes. The bed temperature of the prilled urea was between 51 and 52° C. The dust-free product contained 78.7 wt.-% urea, particles were very smooth and had a faint surface. The product was free of any agglomerates or larger particles.

Example 14

Preparation of a Rumen By-Pass Urea Formulation

The preparation of a rumen by-pass urea formulation was carried out in the same way as described in Example 5 with the exception that a mixture of hydrogenated palm oil and L-tyrosin was used as coating material. A mixture of 94 g of molten hydrogenated palm oil and 31 g of L-tyrosin was coated onto 500 g of prilled urea with a particle size of from 1.8 to 2.4 mm over a time period of 19 minutes. The bed temperature of the urea particles was between 49 and 51° C. The dust-free product contained 80.0 wt.-% urea, the particles very smooth and had a shiny surface. The product was free of agglomerates or larger particles.

Comparative Example 15

Fluidized Bed Coating

The coating was performed in the same way as described in comparative example 7 with the exception that 300 g of prilled urea having a particle size of from 1.8 to 2.4 mm were used. The urea prills were fluidized by air having a temperature of 42° C. Molten hydrogenated palm oil with a melting point of from 50 to 55° C. was heated to 70° C. and sprayed onto the urea prills over a time period of 15 minutes. After addition of 15 wt.-% of hydrogenated palm oil, the product was cooled down by lowering the air temperature.

Comparative Example 16

Drum Coating at Instable Temperature

The coating was performed using the same experimental setup as described in example 5. 400 g of prilled urea with a particle size of from 1.8 to 2.4 mm were placed into the drum coater and then the interior of the drum coater was heated up with hot air until the bed of urea particles had a temperature of 45° C. Molten hydrogenated palm oil with a melting point of from 50 to 55° C. was heated to 60° C. and dropped onto the bed of urea prills at a radial speed of 30 meters per minute over a time period of 25 minutes. The temperature of the bed of urea prills was not stable in this example and ranged from 45 to 60° C. After addition of 15 wt.-% of hydrogenated palm oil, a dust-free product with a large fraction of agglomerates was obtained.

Example 17

Leaching Tests

The products of Examples 5 to 10 were used in leaching tests in McDougall's buffer with pH 6 to simulate in vitro the rumen conditions. The following substances were weighed into a 10 liters bottle:

| | |
|---|---|
| $NaHCO_3$ | 98 g (1.17 mol) |
| $Na_2HPO_4 \cdot 2H_2O$ | 46.3 g (0.26 mol) |
| NaCl | 4.7 g (0.08 mol) |
| KCl | 5.7 g (0.08 mol) |
| $CaCl_2 \cdot 2H_2O$ | 0.4 g (2.7 mmol) |
| $MgCl_2 \cdot 6H_2O$ | 0.6 g (3.0 mmol) |

The solids substances were dissolved in 3 l distilled water. The pH was adjusted to 6 with concentrated hydrochloric acid and the bottle was filled up to a total volume of 10 l. 250 ml of McDougall's buffer were put into Schott flasks with a volume of each 1000 ml, the flasks were sealed, shaken at 100 rotations per minute in a lab shaker (Innova 40, New Brunswick Scientific) and heated to a temperature of about 39° C. 5 g of each of the test substances was added to the flasks and stirred. After 6 hours, the contents of the flasks were filtered off, washed with 50 ml of cold water and dried at 40° C. over night in an oven. The residual product was weighted and the weight loss was considered to be loss in urea.

Calculation of the urea release rate using the formula

Urea release rate=($m$(test product)−$m$(residual product))/($m$(test product*$w$(urea))

Example: m(test product)=5.0 g
m(residual product)=4.2 g
w(urea in test product)=83% urea release rate=(5.00 g−4.20 g)/(5.00 g*0.83)
=19.3%

Results:

TABLE 7

Summary of the results

| Product | RR, 6 h | RR, 24 h | Remarks |
|---|---|---|---|
| Example 5 | 1% | 1% | |
| Comparative example 6 | 100% | 100% | |
| Comparative example 7 | 38% | n.d. | |
| Comparative example 8 | 96% | n.d. | |
| Comparative example 9 | n.d. | n.d. | no particles obtained |
| Example 10 | 1% | 1% | |
| Example 11 | 7% | 65% | |
| Example 12 | 1% | 1% | |
| Example 13 | 7% | 7% | |
| Example 14 | 16% | n.d. | |
| Comparative example 15 | 36% | n.d. | |
| Comparative example 16 | 80% | n.d. | |

RR = release rate
n.d. = not determined

Example 5

Production of by-pass urea with w(urea)=83% by using hydrogenated palm oil in drum coater
SEM pictures show smooth particle surface, no cracks or holes in the coating layer
leaching result: product is rumen by-pass protected Comparative Example 6

Treatment of urea in drum mixer with hydrogenated palm oil, w(urea)=83%
SEM pictures show uneven particle surface, several holes in the coating layer with urea on the surface (bright areas)
leaching result: product is unprotected Comparative Example 7

Treatment of urea in fluidized bed with hydrogenated palm oil, w(urea)=87%
SEM pictures show unround particle surface, surface not very smooth
leaching result: product has sustained release behavior Comparative Example 8

Treatment of urea in drum coater with hydrogenated palm oil, w(urea)=83% at lower temperature
SEM pictures show smooth particle surface but holes and cracks are not filled→self healing was not possible because temperature was too low for a fraction of the fat beeing in the molten stage over longer time
leaching result: product is unprotected Comparative Example 9

Treatment of urea in drum coater with hydrogenated palm oil, w(urea)=83% at higher temperature
no suitable product obtained (see general description)

Example 10

Production of by-pass urea with w(urea)=70% by using hydrogenated palm oil in drum coater
leaching result: product is rumen by-pass protected Example 11

Production of by-pass urea with w(urea)=75,8% by using a mixture of hydrogenated palm oil and CaCO3 in drum coater
SEM pictures show smooth particle surface, no cracks or holes in the coating layer. CaCO3 particles are well dispersed in the coating layer
leaching result: product is rumen by-pass protected Example 12

Production of by-pass urea with w(urea)=76.9% by using hydrogenated palm oil in drum coater
SEM pictures show smooth particle surface, no cracks or holes in the coating layer
leaching result: product is rumen by-pass protected Example 13

Production of by-pass urea with w(urea)=78.9% by using a mixture of hydrogenated palm oil and CaCO3 in drum coater
SEM pictures show smooth particle surface, no cracks or holes in the coating layer
leaching result: product is rumen by-pass protected Example 14

Production of by-pass urea with w(urea)=80.0% by using a mixture of hydrogenated palm oil and L-tyrosine in drum coater
leaching result: product is rumen by-pass protected Comparative Example 15

Treatment of urea in fluidized bed with hydrogenated palm oil, w(urea)=85%
SEM pictures show unround particle surface, holes on surface. self-healing effect not present because particles do not good transfer molten coating material to other particles
leaching result: product has sustained release behavior Comparative Example 16

Treatment of urea in drum coater with hydrogenated palm oil, w(urea)=85% at instable temperature
SEM pictures show not very smooth particle surface, some cracks visible→self healing was not possible because temperature not optimal.
leaching result: product has sustained release behavior The Examples 5, 10 and 12 demonstrate the production of fat coated urea with different loadings of fat.

The Comparative Examples 6, 7 and 15 illustrate methods for the production of products which differ the process of the present invention and these other methods do not give a rumne by-pass product.

The Comparative Examples 8, 9 and 16 demonstrate that the use of other temperature than those according to the present invention do not give rumen by-pass products.

The Examples 11 and 13 demonstrate that suspensions of fat together with inorganic substance can be used in the process of the present invention and give rumen by-pass products.

The Example 14 demonstrates that suspensions of fat together with organic substance can be used in the process of the present invention and give rumen by-pass products.

Example 18

Effects of Oral Administration of a NPN Composition According to the Invention on Fiber Digestibility in a Ruminant The objective of this experiment is to evaluate the effects of various NPN compositions according to the present invention in comparison with traditional NPN compositions, on fiber digestibility in ruminants.

NPN Compositions

The NPN compositions tested are listed in table 8 below.

TABLE 8

| Composition (no) | Type of composition | Content |
|---|---|---|
| 1. | Feed grade urea | 100% urea prills, uncoated |
| 2. | Sustained released urea composition commercially available under the name of Optigen ® 1200. | urea coated with a cross-linked polyester polyurethane coating (as described in U.S. Pat. No. 6,231,895). |
| 3. | Ruminal bypass urea composition | urea prills coated with hydrogenated palm oil |

Treatment Groups

The experiment consists of three experimental groups as set out in Table 9 below. All treatment groups receive an equal amount of urea per day.

TABLE 9

Treatment groups

| Treatment Groups | NPN compositions |
|---|---|
| Group 1 | Holstein bulls (n = 30) receive NPN composition no. 1. |
| Group 2 | Holstein bulls (n = 30) receive NPN composition no. 2. |
| Group 3 | Holstein bulls (n = 30) receive NPN composition no. 3. |

Other experimental parameters including adaptation to the basal diet, animal management, collection of samples, and assessment of fiber digestibility, intake and growth are carried out as set out in Example 1.

Results

The results show that Holstein bulls, which are receiving NPN composition no. 3, 4, 5, 6, or 7 display an increased ability to digest fiber compared to Holstein bulls which are receiving NPN composition no. 1 or no. 2. Therefore, the bulls' ability to digest fiber is improved following treatment with a ruminal bypass NPN composition no. 3, 4, 5, 6, or 7 compared to treatment with a NPN composition that does not allow more than 50% ruminal bypass.

Example 19

Effects of Oral Administration of a Urea Composition According to the Invention on Feed Intake in a Ruminant The experiment is conducted as described under example 5. Feed intake is assessed as set out in Example 2.

Results

The results show that bulls, which are receiving NPN composition no. 3, 4, 5, 6, or 7 display an increased feed intake compared to bulls which are receiving NPN composition no. 1 or 2. Therefore, food intake by the bulls is improved following treatment with a ruminal bypass NPN composition no. 3, 4, 5, 6, or 7 compared to treatment with a NPN composition that does not allow more than 50% ruminal bypass.

Example 20

Effects of Oral Administration of a Urea Composition According to the Invention on Somatic Growth in a Ruminant The experiment is conducted as described under example 5. Somatic growth is assessed according to the following formula:

Somatic growth=[body weight before onset of treatment with a composition as taught herein]−[body weight after termination of the treatment with a composition as taught herein]).

Results

The results show that bulls, which are receiving NPN composition no. 3, 4, 5, 6, or 7 display greater weight gain at the end of the treatment compared to bulls which are receiving NPN composition no. 1 or 2. Therefore, the bulls' ability to gain weight is improved following treatment with a ruminal bypass NPN composition no. 3, 4, 5, 6, or 7 compared to treatment with a NPN composition that does not allow more than 50% ruminal bypass.

Example 21

Effects of Oral Administration of a Urea Composition According to the Invention on Milk Production in a Lactating Ruminant The experiment is conducted as described under example 5, except that the bulls are replace by lactating cows.

Results

The results show that lactating cows which are receiving NPN composition no. 3, 4, 5, 6, or 7 display greater milk production at the end of the treatment compared to lactating cows which are receiving NPN composition no. 1 or 2. Therefore, the lactating cows' ability to produce milk is improved following treatment with a ruminal bypass NPN composition no. 3, 4, 5, 6, or 7 compared to treatment with a NPN composition that does not allow more than 50% ruminal bypass.

Example 22

Assessment of Release Rate of NPN Compound (e.g. Urea)

Materials and Methods

The objective of this study was to determine the disappearance of urea over time from feed grade urea, slow release urea composition (SRU) and bypass urea composition (BPU) samples at fixed time points in order characterize the ruminal disappearance of urea over time. The results obtained can be used as a direct indication of the rate of release of NPN compound in the rumen associated with feed grade urea, SRU and BPU compositions. In order to achieve this goal we have used an in sacco method (also known as the nylon bag method).

The experiment was carried out over a period of 19 days, which included a two-week adaptation period to a basal diet and 5 days for the in sacco urea disappearance assay.

NPN Compositions

The various NPN compositions tested in the present experiment are listed in table 7 above.

Animal Description and Number

Three non-lactating, non-pregnant Holstein heifers were used for the experiment. Heifers were on average 48±0.5 months of age. Each heifer was rumen-cannulated.

Adaptation to the Basal Diet

In order to adapt the animals as well as rumen microbiota to urea consumption, an adaptation period of 14 days was implemented. Specifically, heifers were fed a diet that consisted by low quality hay (7.2% crude protein (CP); 70% neutral detergent fibre (NDF) and 42% acid detergent fibre (ADF)) in addition to 150 g of feed grade urea infused daily directly into the rumen.

Animal Management

Heifers were housed in a tie-stall barn with individual water and feed troughs, rubber mattresses, and wood shaving bedding. The tie-stall was cleaned and the wood shaving replaced daily. Heifers were fed low quality hay ad libitum. In situ incubations occurred during 5 days, in which samples were incubated in the rumen for 0, 0.5, 1, 2, 3, 6, 12 and 24 h.

TABLE 10

Hay composition

| Chemical composition | Hay |
| --- | --- |
| DM (g/Kg) | 873 |
| OM (g/Kg DM) | 945 |
| CP (g/Kg DM) | 72.0 |
| EE (g/Kg DM) | 10.7 |
| NFD (g/Kg DM) | 700 |
| ADF (g/Kg DM) | 421 |
| Lignin (g/Kg DM) | 518 |

Abbreviations:
DM = dry matter,
OM = organic matter,
CP = crude protein,
EE = ether extract,
NDF = neutral detergent fiber,
ADF = acid detergent fiber.

Urea Disappearance Assessment (in Sacco Assay)

In sacco ruminal disappearance of urea was determined to characterize the ruminal release rate of urea in the rumen, which is associated with NPN composition no. 1 to 7 as described above in table 8 above. A sample each NPN compositions no. 1-7 was incubated in each of three ruminally-cannulated Holstein heifers consuming hay (i.e. the samples were directly incubated, in vivo, in the rumen of living Holstein heifers). The time points for duration of the incubation were 0, 0.5, 1, 2, 3, 6, 12 and 24 h.

For each time point, triplicate 10.0 g (urea equivalent) of samples were weighted in polyester bags (R510, 10.6×20 cm, 50 μm pore, Ankom Technology, Macedon, NY), and sealed with a heat sealer. Bags were incubated at 08:00 AM and removed according to the duration of the incubation:

TABLE 11

In sacco ruminal incubation

| Day | Duration (h) | Bags | Incubation time | Removal time |
| --- | --- | --- | --- | --- |
| 1 | 0 | 9 | — | — |
| 1 | 0.5 | 9 | 0800 | 0830 |
| 2 | 1 | 9 | 0800 | 0900 |
| 2 | 2 | 9 | 0800 | 1000 |
| 3 | 3 | 9 | 0800 | 1100 |
| 3 | 6 | 9 | 0800 | 1400 |
| 4 | 12 | 9 | 0800 | 2000 |
| 4 | 24 | 9 | 0800 | — |
| 5 | — | — | — | 0800 |

Upon removal, polyester bags were immediately stored at −20° C. until further analysis. For each polyester bag, a clean plastic funnel was placed in a 250 mL medicine bottle and the frozen polyester bag cut into 4-5 pieces above the funnel. 200 mL of 1M HCl was used to rinse all residues including the bag into the medicine bottle. The bottles were then capped and placed in a 90° C. water bath for 25 minutes in order to dissolve granules into the solution. After incubation, bottles were vigorously agitated and a 10 mL sample of the liquid portion collected. Urea was analyzed by an enzymatic colorimetric test, modified Berthelot method (Human® 10505).

Calculations

The 0 h samples were used to determine the initial urea content in the polyester bags. Urea recovered per mass of sample in each replicate of the assay provided an estimate of the urea content of each sample. The final amount of urea in the in situ residues was determined by multiplying the concentration of the resulting solution by the volume of the solution (mmol/L×L=mmol urea). Percent urea residue was then calculated by expressing the weight (g) of urea remaining in the residue as a percentage of initial urea:

$$\% \text{ Urea residue} = \left(\frac{\text{residual urea (g)}}{\text{inicial urea (g)}}\right) \times 100$$

The data was then plotted as percentage of urea residue over time and fit to the following model adapted from Ørskov and McDonald, J Agr Sci., vol 92: 499-503, (1979).

$$\% \text{ Urea residue} = (U+D) \times \exp^{(-Kd*time)}$$

Where U is the non-released fraction, D is the released fraction and Kd is the release rate of the released fraction.

Bypass fraction of urea was calculated using the escape equation described in Broderick, J Nutr., Vol. 108:181-190, (1978):

$$\text{Bypass \%} = Kp/(Kp+Kd)$$

Where Kd is the release rate and Kp is the passage rate from the rumen to the abomasum. A passage rates of 5%/h were assumed to calculate the bypass fraction (Seo et al., Anim Feed Sci Tech, Vol. 128:67-83, 2006).

Where U is the non-released fraction, D is the released fraction and Kd is the release rate of the released fraction.

Parameters of this model (U, D, kd) were subject to analysis of variance.

Results

Figure 17:
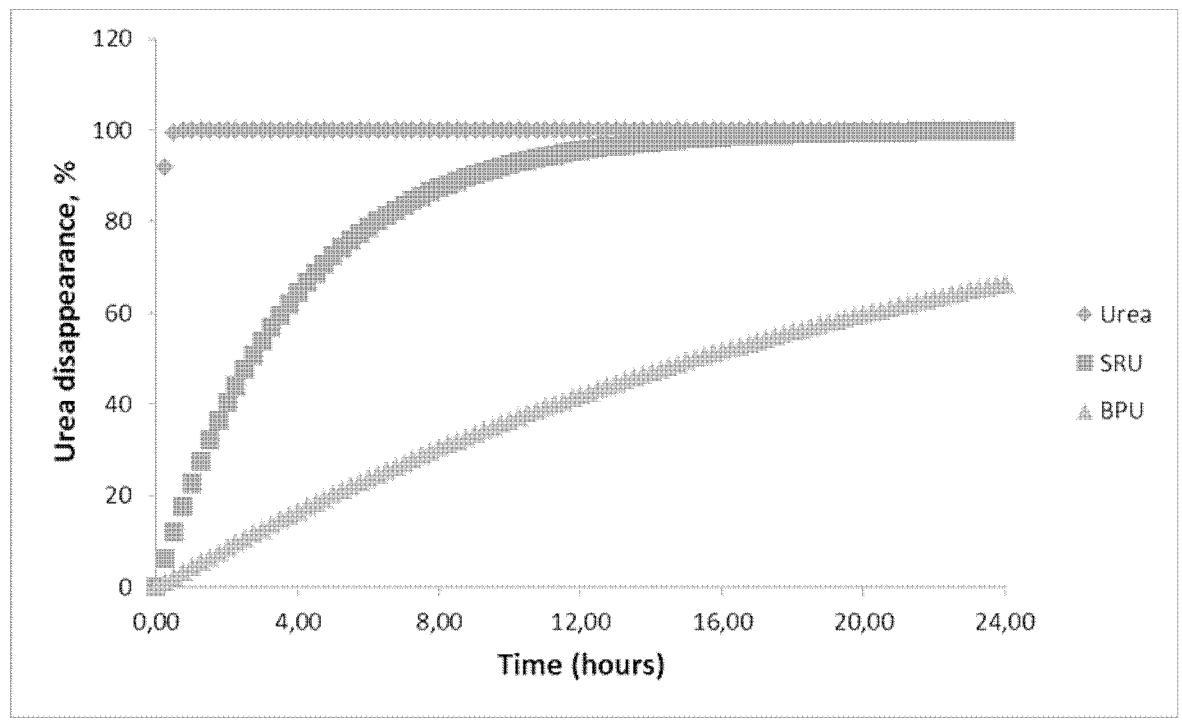
FIG. 17: Ruminal urea disappearance over time of urea, SRU (sustained release urea) BPU (bypass urea).

The results are presented in table 12 and FIG. 17, which shows the ruminal urea disappearance over time of feed grade urea (urea, i.e. NPN composition no.1), sustained release urea (SRU, i.e. NPN composition no. 2) and bypass urea (BPU, i.e. curve representing the average for NPN compositions no. 3-7). It can be observed that NPN compositions no. 3-9 differ from NPN compositions no.1 and no.2 on all parameters shown in table 11. Specifically, it can be observed that the NPN compositions no. 3-7 all display a release rate of urea that is less than 5% per hour as well as a bypass fraction of NPN that is greater than 50% compared to NPN compositions no. 1 and 2. These results indicate that NPN composition according to the present invention (e.g. NPN compositions no. 3-7) have a different release site in the ruminant gastrointestinal tract, i.e. post-rumen release compared to conventional NPN compositions, e.g. NPN compositions no. 1 and 2.

TABLE 12

Ruminal urea disappearance from feed grade urea, SRU and BPU.

| Parameter | Urea (no. 1) | SRU (no. 2) | BPU (no. 3) |
|---|---|---|---|
| U (%) | 1.30 | 27.3 | 53.7 |
| D (%) | 98.7 | 72.7 | 46.3 |
| Kd (rate, %/h) | 999 | 25.8 | 4.55 |
| Bypass fraction (%) | 0.49 | 17.3 | 58.5 |

Example 23

Ruminal and Post-Ruminal Urea Release from Protected Urea Sources

The objective of this study was to demonstrate that a sustained release urea composition provided delayed urea release in the rumen while a ruminal bypass urea composition as taught herein was substantially rumen resistant and substantially post-ruminally digestible, and provided urea release post-ruminally.

Materials and Methods

The NPN compositions tested are described in table 13 below:

TABLE 13

List of NPN compositions tested.

| Composition (no) | Type of composition | Content |
|---|---|---|
| 1. | Feed grade urea | 100% urea prills, uncoated |
| 2. | Sustained released urea composition commercially available under the name of Optigen ® 1200. | urea coated with a cross-linked polyester polyurethane coating (as described in U.S. Pat. No. 6,231,895). |
| 3. | Ruminal bypass urea composition | urea prills coated with hydrogenated palm oil. |

The experiment was carried out over a period of 26 days, which included a two-week adaptation period to a basal diet and three experimental periods of four days each to evaluate ruminal and post-ruminal urea release.

Animal Description and Number

Three non-lactating, non-pregnant Holstein heifers were used for the experiment. The Holstein heifers were on average 48±0.5 months of age and weighed on average 800 kg. Each heifer was rumen-cannulated. The experimental design was a 3×3 Latin Square, involving 3 treatments, 3 periods and 3 animals. Experimental unit is the combination animal×period, totalizing 9 experimental units.

Treatments

The experiment consisted of 3 treatment regimens (i.e. treatment groups 1, 2, and 3). Specifically, each treatment group differed with respect to the NPN composition they received. Treatment groups received an equal amount of 70.5 g of non-protein nitrogen per day, i.e., 150 g of urea.

TABLE 14

Treatment groups

| Treatment Groups | Treatment Regimens |
|---|---|
| Treatment 1: Urea (non-coated) | Holstein heifers (n = 3) received NPN composition no. 1 (see table 13) |
| Treatment 2: Sustained release urea (SRU) | Holstein heifers (n = 3) received NPN composition no. 2 (see table 13) |
| Treatment 3: Bypass urea (BPU) | Holstein heifers (n = 3) received NPN composition no. 3 (see table 13) |

Adaptation to the Basal Diet

In order to adapt the animals as well as rumen microbiota to urea consumption, an adaptation period of 14 days was implemented. Specifically, heifers were fed a diet that consisted by low quality hay (7.2% CP; 70% NDF and 42% ADF) in addition to 150 g feed grade urea/day.

Animal Management

Heifers were housed in a tie-stall barn with individual water and feed troughs, rubber mattresses, and wood shaving bedding. The tie-stall was cleaned and the wood shaving replaced daily. Heifers were fed low quality hay ad libitum. Each experimental period last 4 days in which test products were infused in the rumen (day one) and samples were taken on the following 48 h. Days three and four are defined as washout periods and feed grade urea (150 g) were provided for all heifers during this period.

TABLE 15

Infusion site and composition

| | Day within period | | | |
|---|---|---|---|---|
| Treatment | Day 1 | Day 2 | Day 3 | Day 4 |
| Urea (non-coated) | Urea into rumen | — | Urea into rumen | Urea into rumen |
| SRU | SRU into rumen | — | Urea into rumen | Urea into rumen |
| BPU | BPU into rumen | — | Urea into rumen | Urea into rumen |

TABLE 16

Hay composition

| Chemical composition | Hay |
|---|---|
| DM (g/Kg) | 873 |
| OM (g/Kg DM) | 945 |

TABLE 16-continued

Hay composition

| Chemical composition | Hay |
|---|---|
| CP (g/Kg DM) | 72.0 |
| EE (g/Kg DM) | 10.7 |
| NFD (g/Kg DM) | 700 |
| ADF (g/Kg DM) | 421 |
| Lignin (g/Kg DM) | 518 |

DM = dry matter,
OM = organic matter,
CP = crude protein,
EE = ether extract,
NDF = neutral detergent fiber,
ADF = acid detergent fiber.

Ruminal and Post-Ruminal Release and Assessment

On the 1st day of each experimental period, 150 g (urea equivalent) were infused into the rumen through a rumen cannula at 0800, for each treatment group. Rumen fluid samples were taken at 0, 0.5, 1, 2, 3, 6, and 12 h post-infusion through a tube adapted to the rumen cannula. For ammonia nitrogen quantification, a volume of 8 mL was acidified with 200 μL of H2SO4 7.2N (in duplicate), labelled (study code, period, animal, hour) and frozen (−20° C.). Ruminal ammonia nitrogen was analyzed by an indophenol catalysed colorimetric reaction (Chaney and Marbach, Clin. Chem., Vol 8: 130-132, 1962).

Faecal Collection and Sampling

On the first and second day of experimental period, faeces were collected during 48 h. During this period wood shaves were withdrawn from the mattresses. On day 1, before the ruminal infusion of tested articles, a baseline sample was taken directly from the rectum of each animal. From the moment of ruminal incubation, total faeces were collected for 48 hours. During collection days, faeces were well homogenized, weighted, and a sub-sample (≈200 g) taken on the following hours of the day: 0800 (only for day 2) 1100, 1500 and 1900. Samples were labelled (study code, period, animal, hour) and frozen at −20° C. for posterior analysis of dry matter and nitrogen.

Results

Figure 18:
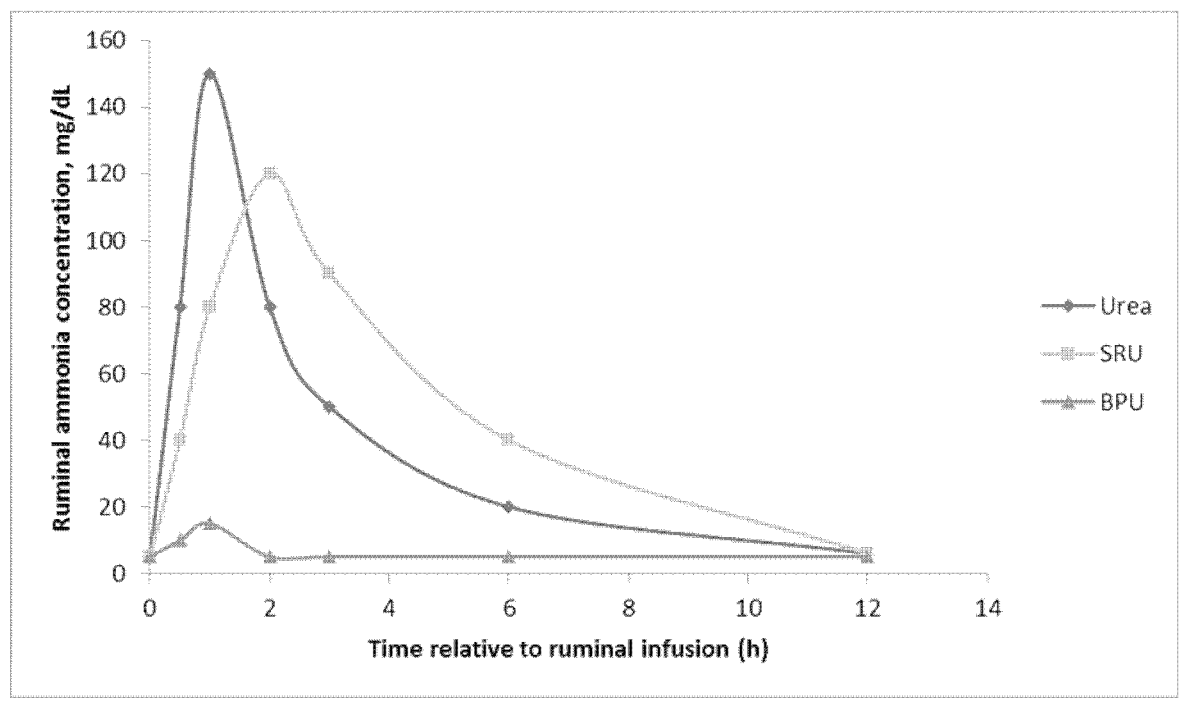
FIG. 18: Ruminal ammonia concentrations (mg/dL) relative to time of infusion. SRU=Slow release urea; BPU=Bypass urea.

The results of the experiment are shown in FIG. 18. The results show that the ruminal ammonia concentration (Y axis), over time (X axis), was higher (P<0.05) when urea (i.e. NPN composition no. 1) or SRU (i.e. NPN composition no. 2) was infused into rumen as compared to when BPU (i.e. composition no. 3) was infused in the rumen.

The results further demonstrated that SRU (i.e. NPN composition no. 2) had a delayed ruminal urea release in comparison to the pattern of urea release associated with non-coated feed grade urea (i.e. NPN composition no. 1). Only a small increase in ruminal ammonia nitrogen levels (mg/dl) was observed with BPU (i.e. NPN composition no. 3), over time. This indicates that BPU is released in the rumen to a much lower extent than SRU or immediate release (non-coated) urea.

Results on post-ruminal release and absorption are presented in Table 17. Nitrogen (N) digestibility was similar for food grade urea (NPN composition no. 1) and BPU (NPN composition no. 3). N intake was higher in ruminants fed BPU. The N excretion in the faeces was slightly higher in BPU compared to food grade urea, likely as a result of higher N intake. In addition, N excretion through urine was 20.3% lower when BPU was provided in comparison with feed grade urea. Relative N retention (g of N retained per gram of ingested N) was 32.9% and 19.9% higher for BPU as compared to Urea and SRU, respectively, indicating that more nitrogen is utilized by the animals when BPU is provided.

TABLE 17

Nitrogen intake, faecal N excretion and N digestibility after ruminal infusion of urea, SRU and BPU.

| | Treatments[1] | | |
|---|---|---|---|
| | Urea | SRU | BPU |
| N Intake (g)[2] | 307.58 | 303.97 | 325.09 |
| N excretion faeces (g)[3] | 119.92 | 128.94 | 128.08 |
| N excretion urine (g)[4] | 108.30 | 87.293 | 86.291 |
| Total N excretion (g)[5] | 228.22 | 216.23 | 214.37 |
| N digestibility (%)[6] | 61.81 | 57.48 | 60.93 |
| Relative N retention (g/g)[7] | 0.2572 | 0.2851 | 0.3418 |

[1]SRU = Slow release urea; BPU = By pass urea;
[2]Total N intake in 48 h including N infusion into rumen;
[3]Faecal N excretion during the 48 hours following N infusion into rumen;
[4]Urinary N excretion during the 48 hours following N infusion into rumen;
[5]Total N excretion (Faecal N excretion + Urinary N excretion);
[6]((N intake − N excreted)/N intake) * 100;
[7](1 − (N excreted/N intake)).

The invention claimed is:

1. A method for feeding a ruminant, the method comprising:
providing to the ruminant a composition for consumption, wherein the composition comprises:
a non-protein nitrogen compound, and
a rumen by-pass agent, for ruminally by-passing the non-protein nitrogen compound,
wherein the rumen by-pass agent is a coating surrounding the non-protein nitrogen compound and the coating consists essentially of a hydrogenated vegetable oil,
the non-protein nitrogen compound is one or more compounds selected from the group consisting of urea, ammonium salts, methylene urea, biuret, acetamide, butyramide, dicyanoamide, formamide, ethylene urea, isobutanol diurea, lactosyl urea, propionamide, uric acid and urea phosphate,
a ratio of the non-protein nitrogen compound to the coating is from 83:17 to 75:25 by weight,
wherein the composition does not comprise any cracks, breaks, or flaws in the coating, and
wherein the providing results in a ruminal bypass fraction of the non-protein nitrogen compound of at least 50% in the ruminant.

2. The method according to claim 1, wherein the hydrogenated vegetable oil is selected from the group consisting of hydrogenated palm oil, soybean oil, cotton seed oil, rapeseed oil, canola oil, peanut oil, corn oil, olive oil, sunflower oil, safflower oil, coconut oil, linseed oil, tong oil, and castor oil.

3. The method according to claim 1, wherein the non-protein nitrogen compound is one or more compounds selected from the group consisting of ammonium acetate, ammonium sulfate, ammonium butyrate and an ammonium salt of an amino acid.

4. The method according to claim 1, wherein the composition has an average particle size of about 1 mm to about 6 mm.

5. The method of claim 1, further comprising:
feeding the ruminant simultaneously with at least one feed selected from the group consisting of corn, silage, alfalfa silage, mixed hay, and grains.

6. The method of claim 1, wherein an amount of the composition administered is 0.0001% to 1% of the ruminant's body weight.

7. The method of claim 1, wherein the method increases somatic growth in the ruminant.

8. The method of claim 1, wherein the method increases feed intake in the ruminant.

9. The method of claim 1, wherein the method reduces nitrogen excretion in the ruminant.

10. The method of claim 1, wherein the method increases rumen pH stability in the ruminant.

11. The method of claim 1, wherein the method reduces ammonia toxicity in the ruminant.

12. The method of claim 1, wherein particles of the composition are not agglomerated.

13. The method of claim 1, wherein the ruminal bypass fraction of the non-protein nitrogen compound is at least 80% in the ruminant.

14. The method of claim 1, wherein a rate of release of the non-protein nitrogen compound in the rumen of the ruminant is less than 5% per hour.

15. The method of claim 1, wherein the composition is made by a process comprising:
heating particles in a drum coater at a temperature in a range from 10° C. below a lower limit of a melting range of the rumen by-pass agent to the lower limit of the melting range of the rumen by-pass agent to form heated particles, the particles comprising the non-protein nitrogen compound;
heating the rumen by-pass agent at a temperature in a range from an upper limit of the melting range of the rumen by-pass agent and 10° C. above the upper limit of the melting range of the rumen by-pass agent outside of the drum coater to form a heated rumen by-pass agent; and
applying the heated rumen by-pass agent to the heated particles in the drum coater to form the coating on the particles.

16. The method of claim 15, wherein the rumen by-pass agent has a difference between the lower and the upper limit of the melting range of from 3° C. to 10° C.

17. The method of claim 15, wherein the temperature of the heated rumen by-pass agent is between about 50° C. and about 85° C.

18. The method of claim 15, wherein the temperature of the heated particles is between 40° C. and about 75° C.

* * * * *